(12) United States Patent
Hata

(10) Patent No.: US 10,851,194 B2
(45) Date of Patent: Dec. 1, 2020

(54) (METH)ACRYLIC SILICONE GRAFT COPOLYMER AND A METHOD FOR PREPARING THE SAME

(71) Applicant: SHIN-ETSU CHEMICAL CO., LTD., Tokyo (JP)

(72) Inventor: Ryunosuke Hata, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 0 days.

(21) Appl. No.: 16/270,060

(22) Filed: Feb. 7, 2019

(65) Prior Publication Data

US 2019/0248945 A1 Aug. 15, 2019

(30) Foreign Application Priority Data

Feb. 9, 2018 (JP) .................. 2018-022099

(51) Int. Cl.
| | |
|---|---|
| *C08F 290/06* | (2006.01) |
| *C08F 230/08* | (2006.01) |
| *A61K 8/895* | (2006.01) |
| *C08L 51/08* | (2006.01) |
| *A61Q 19/00* | (2006.01) |

(Continued)

(52) U.S. Cl.
CPC .......... *C08F 290/068* (2013.01); *A61K 8/893* (2013.01); *A61K 8/895* (2013.01); *A61Q 19/00* (2013.01); *C08F 2/38* (2013.01); *C08F 220/14* (2013.01); *C08F 230/08* (2013.01); *C08F 283/124* (2013.01); *C08L 51/085* (2013.01);
(Continued)

(58) Field of Classification Search
CPC ....... C08F 30/08; C08F 130/08; C08F 230/08
See application file for complete search history.

(56) References Cited

U.S. PATENT DOCUMENTS

| 4,970,252 A | 11/1990 | Sakuta | |
|---|---|---|---|
| 5,171,809 A * | 12/1992 | Hilty | ........................ C08F 30/08 526/190 |

(Continued)

FOREIGN PATENT DOCUMENTS

| JP | 1932769 | 2/1989 |
|---|---|---|
| JP | H09-136813 A | 5/1997 |

(Continued)

OTHER PUBLICATIONS

Gabor, Allen H. et al., "Group-Transfer Polymerization of tert-Butyl Methacrylate and [3-(Methacryloxy)propyl] pentamethyldisiloxane: Synthesis and Characterization of Homopolymers and Random and Block Copolymers"; Chemistry of Materials (1996), vol. 8, No. 9, pp. 2272-2281.

(Continued)

*Primary Examiner* — Marc S Zimmer
(74) *Attorney, Agent, or Firm* — Rimon, P.C.

(57) ABSTRACT

A (meth)acrylic silicone graft (co)polymer having a unit represented by the following formula (I), a structure represented by the following formula (III) at one terminal, and a structure represented by the following formula (IV) at the other terminal,

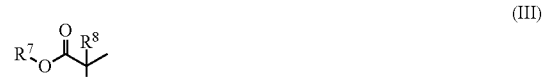

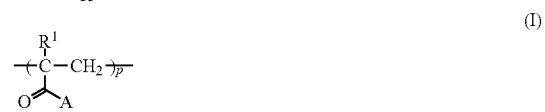

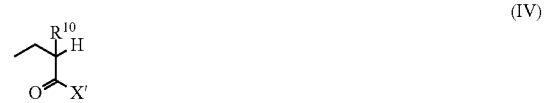

wherein A is a group having a linear organopolysiloxane structure represented by the following formula (1) or a group having a dendritic organopolysiloxane structure represented by the following formula (2-1) or (2-2), X' is a group as defined for A,

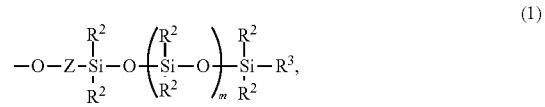

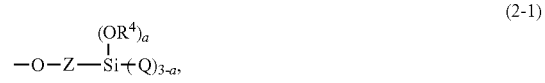

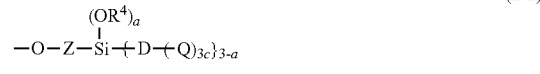

wherein Z is a divalent organic group, Q is a group represented by the following formula (2), D is a $(3^c+1)$-valent organopolysiloxanyl group which has a hierachial order of c, $3^c$ means 3 raised to the power of c, c is an integer of from 1 to 8.

Q

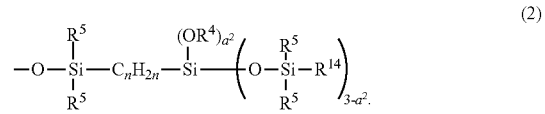

8 Claims, 2 Drawing Sheets

(51) Int. Cl.
  *A61K 8/893*   (2006.01)
  *C08F 283/12*  (2006.01)
  *C08F 220/14*  (2006.01)
  *C08F 2/38*    (2006.01)

(52) U.S. Cl.
  CPC ...... *A61K 2800/10* (2013.01); *C08F 2438/01* (2013.01)

(56) References Cited

U.S. PATENT DOCUMENTS

| | | | |
|---|---|---|---|
| 5,236,986 A | 8/1993 | Sakuta | |
| 5,258,490 A * | 11/1993 | Chang | A61L 15/24 523/103 |
| 5,314,960 A * | 5/1994 | Spinelli | C08F 287/00 525/280 |
| 2003/0052424 A1 | 3/2003 | Turner et al. | |
| 2003/0199660 A1 | 10/2003 | Sakuta | |
| 2004/0209973 A1 * | 10/2004 | Steffen | G02B 1/043 523/107 |
| 2004/0234477 A1 | 11/2004 | Sakuta | |
| 2004/0253197 A1 | 12/2004 | Sakuta | |

FOREIGN PATENT DOCUMENTS

| | | |
|---|---|---|
| JP | 2631772 B2 | 7/1997 |
| JP | 2767633 B2 | 6/1998 |
| JP | 2976146 B2 | 11/1999 |
| JP | 2001-342255 A | 12/2001 |
| JP | 2005520703 A | 7/2005 |
| JP | 2009-046662 A | 3/2009 |
| JP | 2009-185296 A | 8/2009 |
| JP | 2012-072081 A | 4/2012 |
| WO | WO 03/020828 A1 | 3/2003 |
| WO | WO 03/024413 A1 | 3/2003 |
| WO | WO-2005/031400 A2 * | 4/2005 |

OTHER PUBLICATIONS

Extended European Search Report for Application No. 19156142.2, dated Jul. 22, 2019.

* cited by examiner

(METH)ACRYLIC SILICONE GRAFT COPOLYMER AND A METHOD FOR PREPARING THE SAME

CROSS REFERENCE

This application claims the benefits of Japanese Patent Application No. 2018-022099 filed on Feb. 9, 2018, the contents of which are hereby incorporated by reference.

FIELD OF THE INVENTION

The present invention relates to a (meth)acrylic silicone graft copolymer, a method for preparing the (meth)acrylic silicone graft copolymer, and a cosmetic containing the (meth)acrylic silicone graft copolymer.

A (meth)acrylic silicone graft copolymer forms a film being highly water repellent, flexible and highly adhesive and, therefore, is widely used in cosmetics. For instance, Patent Literatures 1 to 4 describe (meth)acryl silicone graft copolymers.

Monomers such as methyl methacrylate used in the synthesis of (meth)acrylic silicone graft copolymers are known to irritate a skin and eyes, and are removed from the polymer by vacuum stripping or washing. The (meth)acrylic polymer synthesized using a conventional radical polymerization initiator such as a peroxide or azo type initiator contains a polymer having a double bond at the terminal. The latter decomposes thermally around 150 degrees C. to form monomers by a reverse reaction. Therefore, removal of monomers, particularly those having high boiling points, is difficult in conventional techniques.

On the other hand, when a (meth) acrylic silicone graft copolymer containing monomers is blended in a cosmetic, irritation on a skin and undesirable odor may occur and, accordingly, high purification is desired. Further, a (meth) acrylic silicone graft copolymer obtained by polymerization using a conventional radical initiator has problems such that a hydrogen atom is withdrawn from the polymer chain by the initiator to cause crosslinking, resulting in stickiness on a cosmetic film.

PRIOR LITERATURES

Patent Literature 1: Japanese Patent Application Laid-Open No. 2009-46662
Patent Literature 2: Japanese Patent Application Laid-Open No. 2012-72081
Patent Literature 3: Japanese Patent No. 2767633
Patent Literature 4: Japanese Patent No. 2976146

SUMMARY OF THE INVENTION

One of the purposes of the present invention is to provide a highly pure (meth)acrylic silicone graft copolymer which has a higher heat resistance and contains a smaller amount of monomers. Another purpose of the present invention is to provide a cosmetic which has less stickiness and good make-up retention.

The present inventors have made research and found that improved heat resistance is attained in a (meth)acrylic silicone graft copolymer which has a unit represented by the following formula (I), a structure represented by the following formula (III) at one terminal and a structure represented by the following formula (IV) at the other terminal, because the copolymer has no unsaturated bond at the terminals.

Thus, the present invention provides a (meth)acrylic silicone graft (co)polymer having a unit represented by the following formula (I), a structure represented by the following formula (III) at one terminal, and a structure represented by the following formula (IV) at the other terminal,

wherein $R^1$ is, independently of each other, a hydrogen atom or a methyl group, $R^7$ is an alkyl group having 1 to 4 carbon atoms, $R^8$ and $R^9$ are, independently of each other, a hydrogen atom or an alkyl group having 1 to 4 carbon atoms, $R^{10}$ is a hydrogen atom or a methyl group, A is a group having a linear organopolysiloxane structure represented by the following formula (1) or a group having a dendritic organopolysiloxane structure represented by the following formula (2-1) or (2-2), X' is a group as defined for A, and p is an integer such that the (co)polymer has a number average molecular weight of 1,000 to 1,000,000 g/mol,

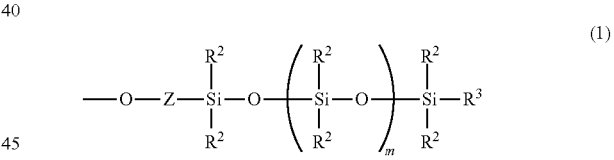

wherein Z is a divalent organic group, $R^2$ is a saturated hydrocarbon group having 1 to 10 carbon atoms or a phenyl group, $R^3$ is a saturated hydrocarbon group having 1 to 10 carbon atoms, and m is an integer of from 0 to 100,

wherein Z is a divalent organic group, a is a number of 0 to 3, Q is a group represented by the following formula (2), D is a $(3^c+1)$-valent organopolysiloxanyl group which has a hierachial order of c, 3' means 3 raised to the power of c, c is an integer of from 1 to 8,

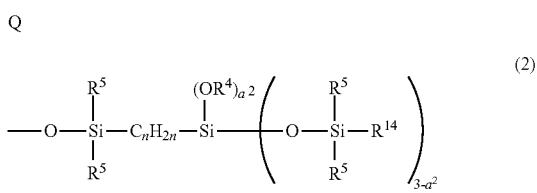

wherein $R^4$ is a saturated hydrocarbon group having 1 to 10 carbon atoms or a phenyl group, $R^5$ is a saturated hydrocarbon group having 1 to 6 carbon atoms or a phenyl group, $R^{14}$ is a hydrogen atom, a saturated hydrocarbon group having 1 to 10 carbon atoms or a phenyl group, $a^2$ is the number of 0 to 2, and n is an integer of from 2 to 12.

Further, the present invention provides a (meth)acrylic silicone graft copolymer having a unit represented by the following formula (I), a unit represented by the following formula (II), a structure represented by the following formula (III) at one terminal and a structure represented by the following formula (IV) at the other terminal,

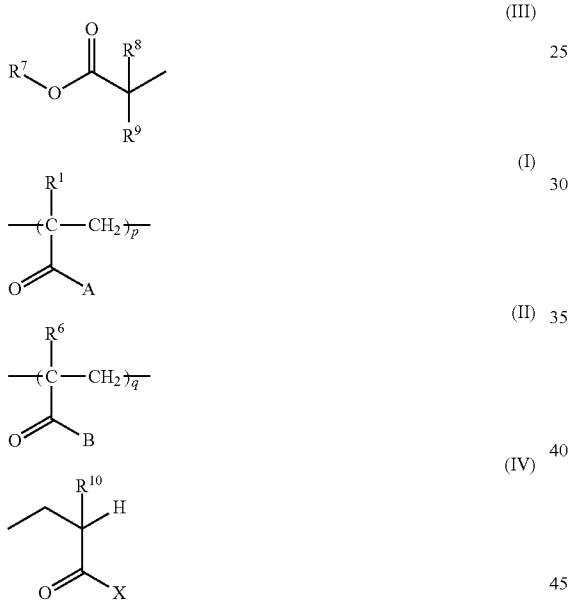

wherein $R^6$ are, independently of each other, a hydrogen atom or a methyl group, $R^1$, $R^7$, $R^8$, $R^9$ and $R^{10}$ are as define above, A is as defined above, B is an alkoxy group which has 1 to 20 carbon atoms, an aryloxy group having 6 to 20 carbon atoms, an amino group, a siloxy group, a halogen atom, a hydroxyl group or a substituted or unsubstituted, monovalent hydrocarbon group which has 1 to 20 carbon atoms and may have at least one selected from —O—, —S— and —NR—, wherein R is a hydrogen atom or a monovalent hydrocarbon group having 1 to 20 carbon atoms, provided that the oxygen atom, the sulfur atom and the nitrogen atom are not adjacent to each other, and X is a group as defined for A or B, an order of the units (I) and (II) is not limited, p is an integer of 1 or larger, q is an integer of 1 or larger, and p+q is the number such that the copolymer has a number average molecular weight of 1,000 to 1,000,000 g/mol.

Additionally, the present invention provides a method for preparing the aforesaid two types of the (meth)acrylic silicone graft (co)polymer and a cosmetic containing the (meth) acrylic silicone graft (co)polymer.

The present (meth)acrylic silicone graft (co)polymer has an excellent heat resistance and a high purity. A cosmetic comprising the present (meth)acrylic silicone graft (co) polymer has less stickiness and good make-up retention.

DETAILED DESCRIPTION OF THE INVENTION

Figure 1:
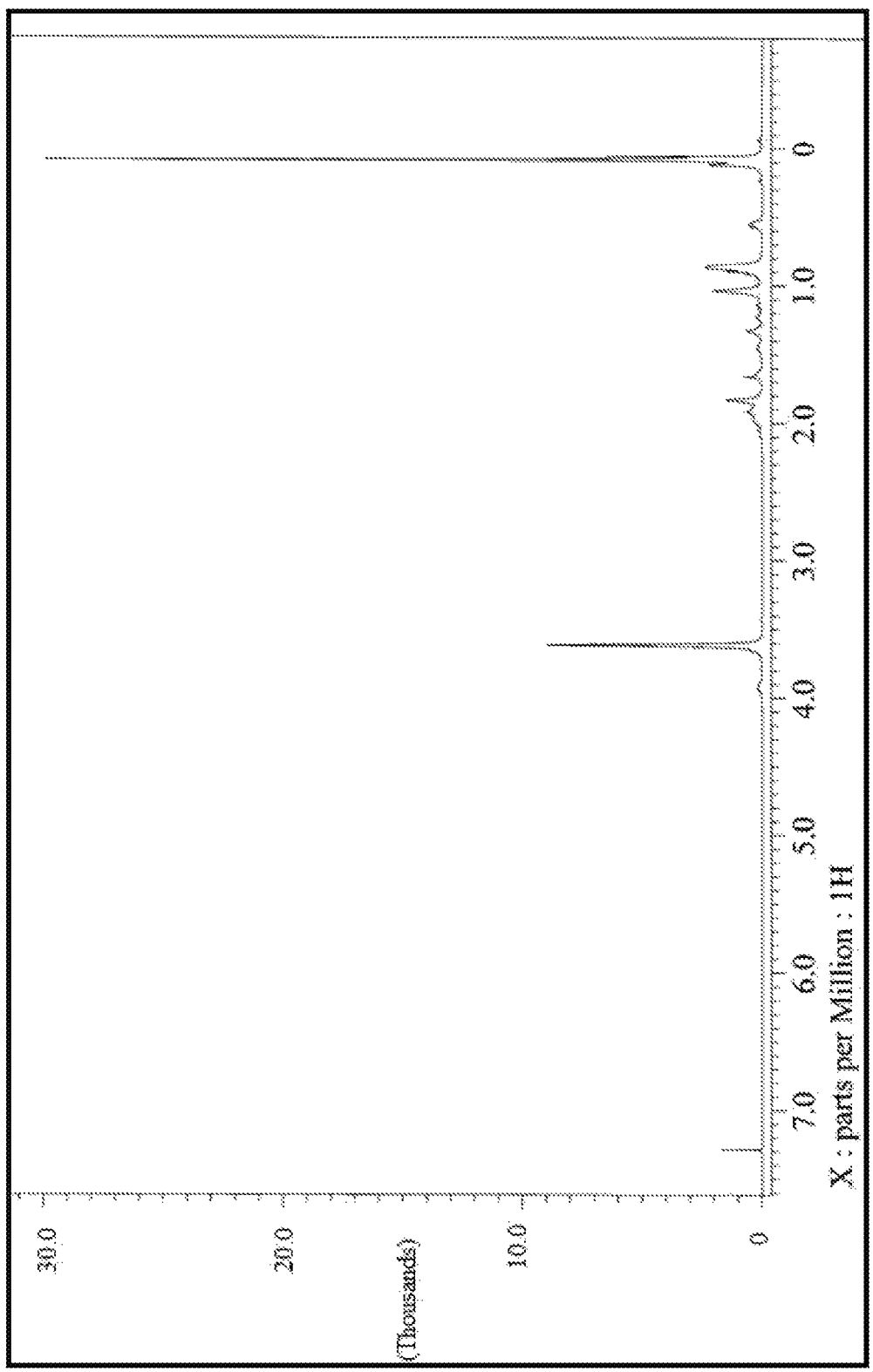
FIG. 1 is an overall view of $^1$H-NMR spectra of the copolymer prepared in Example 1.

The present invention will be described below in more detail. In the following description, methacryl and acryl are referred to as "(meth) acryl". Methacrylic ester and acrylic ester are referred to as "(meth) acrylate".

The present invention provides a (meth)acrylic silicone graft (co)polymer which essentially has a unit represented by the following (I), preferably further has a unit represented by the following (II). The present (meth)acrylic silicone graft (co)polymer is characterized by having a structure represented by the following (III) at one terminal and a structure represented by the following (IV) at the other terminal. The (co)polymer has no unsaturated bond at any terminal and, therefore, has excellent heat resistance and thermal decomposition is prevented. Thus, a temperature at which loss of the weight of the (co)polymer in a nitrogen atmosphere is 50%, hereinafter referred to as 50% weight loss temperature, is 360 degrees C. or higher. In the present invention, the 50% weight loss temperature is a temperature at which loss of the weight of the copolymer reached a half of the initial weight in a determination with a thermogravimetric analyzer. The loss of the weight is determined during raising a temperature from 0 degrees C. to 10 degrees C. per minute in a nitrogen atmosphere.

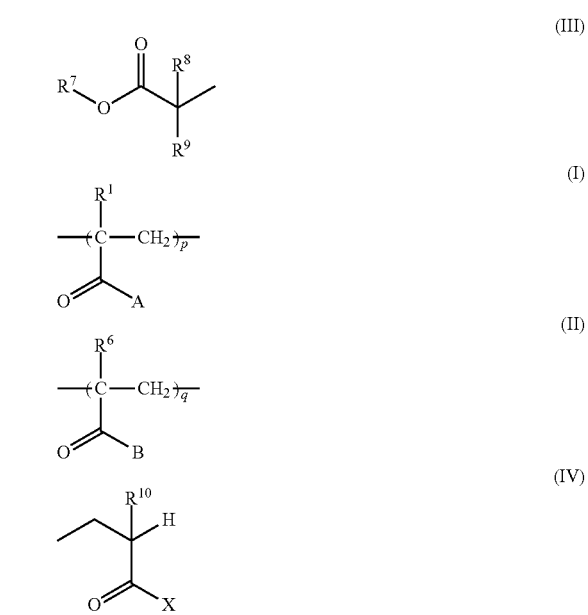

wherein $R^1$ and $R^6$ are, independently of each other, a hydrogen atom or a methyl group, $R^7$ is an alkyl group having 1 to 4 carbon atoms, $R^8$ and $R^9$ are, independently of each other, a hydrogen atom or an alkyl group having 1 to 4 carbon atoms, $R^{10}$ is a hydrogen atom or a methyl group, B is an alkoxy group which has 1 to 20 carbon atoms, an aryloxy group having 6 to 20 carbon atoms, an amino group, a siloxy group, a halogen atom, a hydroxyl group or a substituted or unsubstituted, monovalent hydrocarbon group which has 1 to 20 carbon atoms and may have at least one selected from —O—, —S— and —NR—, wherein R is a hydrogen atom or a monovalent hydrocarbon group having 1 to 20 carbon atoms, provided that the oxygen atom, the sulfur atom and the nitrogen atom are not adjacent to each other, and X is a group as defined for A or B.

In the unit (I), A is a group having a linear organopolysiloxane structure represented by the following formula (1) or a group having a dendritic organopolysiloxane structure represented by the following formula (2-1) or (2-2).

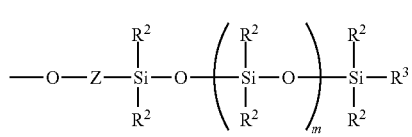

(1)

wherein Z is a divalent organic group, $R^2$ is a saturated hydrocarbon group having 1 to 10 carbon atoms or a phenyl group, $R^3$ is a saturated hydrocarbon group having 1 to 10 carbon atoms, and m is an integer of from 0 to 100,

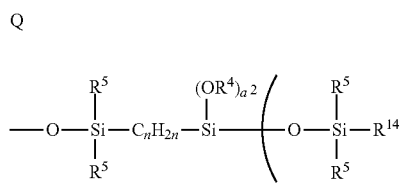

(2-1)

(2-2)

wherein Z is a divalent organic group, a is a number of 0 to 3, Q is a group represented by the following formula (2), D is a $(3^c+1)$-valent organopolysiloxanyl group having a dendritic structure which has a hierachial order of c, $3^c$ means 3 raised to the power of c, c is an integer of from 1 to 8,

Q

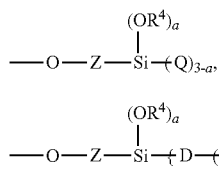

(2)

wherein $R^4$ is a saturated hydrocarbon group having 1 to 10 carbon atoms or a phenyl group, $R^5$ is a saturated hydrocarbon group having 1 to 6 carbon atoms or a phenyl group, $R^{14}$ is a hydrogen atom, a saturated hydrocarbon group having 1 to 10 carbon atoms or a phenyl group, $a^2$ is the number of 0 to 2, and n is an integer of from 2 to 12.

In the formula (1), Z is a divalent organic group, preferably a divalent saturated hydrocarbon group having 2 to 12 carbon atoms, more preferably a propylene group. $R^2$ is a saturated hydrocarbon group having 1 to 10 carbon atoms or a phenyl group, preferably a saturated hydrocarbon group having 1 to 5 carbon atoms, more preferably a methyl group. $R^3$ is a saturated hydrocarbon group having 1 to 10 carbon atoms, preferably a saturated hydrocarbon group having 1 to 5 carbon atoms, more preferably a methyl group. m is an integer of 0 to 100, preferably an integer of 1 to 60, and more preferably an integer of 5 to 30.

In the formulas (2-1) and (2-2), $R^4$ is a saturated hydrocarbon group having 1 to 10 carbon atoms or a phenyl group, preferably a saturated hydrocarbon group having 1 to 5 carbon atoms, and more preferably a methyl group. $R^5$ is a saturated hydrocarbon group having 1 to 6 carbon atoms or a phenyl group, preferably a saturated hydrocarbon group having 1 to 3 carbon atoms, and more preferably a methyl group. Z is a divalent organic group, preferably a saturated hydrocarbon group having 1 to 10 carbon atoms, and more preferably a saturated hydrocarbon having 1 to 5 carbon atoms. D is a $(3^c+1)$-valent organopolysiloxanyl group having a dendritic structure which has a hierachial order of c, $3^c$ means 3 raised to the power of c, c is an integer of from 1 to 8, preferably an integer of from 1 to 4, more preferably an integer of 1 to 2.

The group represented by the formula (2-1) or (2-2) is represented by the following structure in detail.

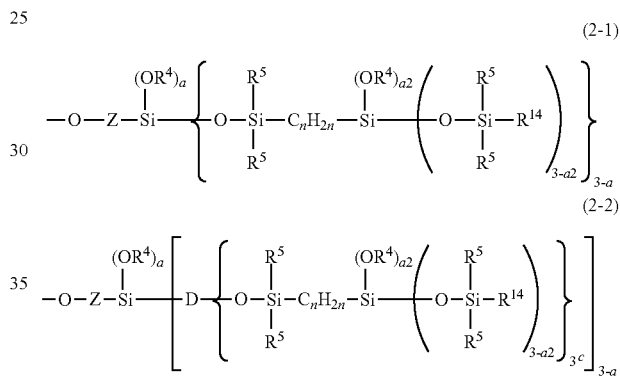

In the formula (2-2), D is represented, for example, by the following structure.

D is the following $(3^1+1)$-valent organopolysiloxanyl group having a dendritic structure which has hierachial order (c) is 1.

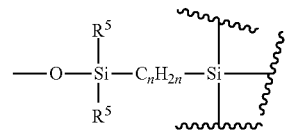

D is the following $(3^2+1)$-valent organopolysiloxanyl group having a dendritic structure which has hierachial order (c) is 2.

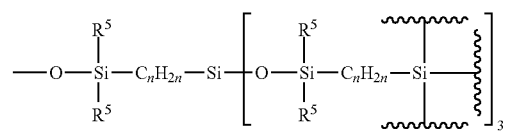

D is the following $(3^3+1)$-valent organopolysiloxanyl group having a dendritic structure which has hierachial order (c) is 3.

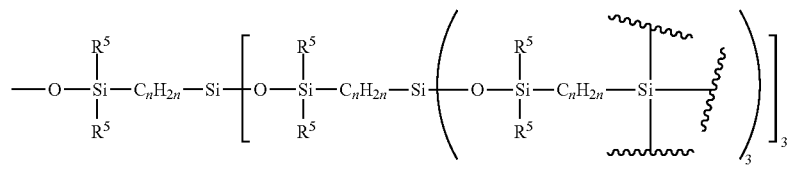

Examples of the group represented by A include the following groups.

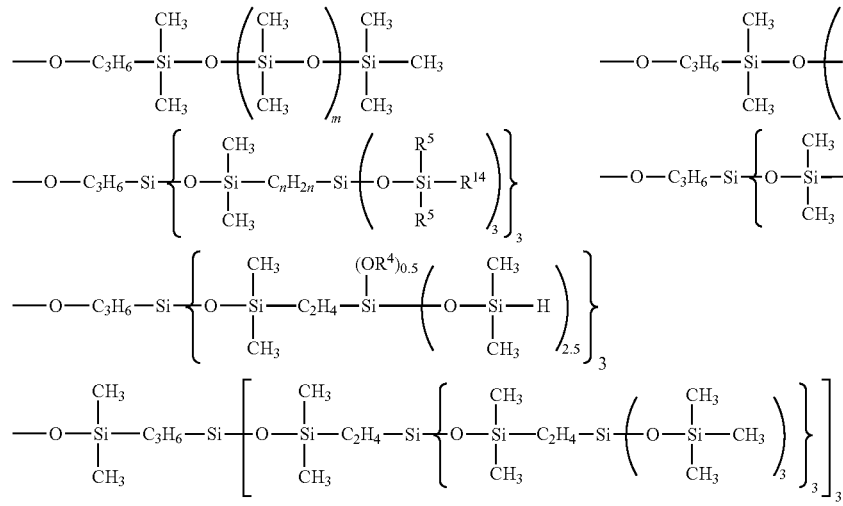

wherein D is the $(3^1+1)$-valent organopolysiloxanyl group having a dendritic structure which has hierachial order (c) is 1.

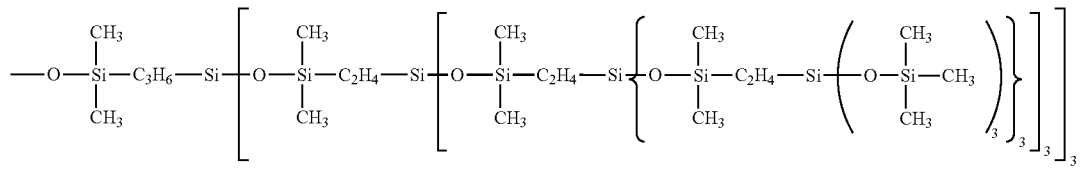

wherein D is the $(3^2+1)$-valent organopolysiloxanyl group having a dendritic structure which has hierachial order (c) is 2.

In the unit (II), $R^6$ is a hydrogen atom or a methyl group. B is selected from an alkoxy group having 1 to 20 carbon atoms, an aryloxy group having 6 to 20 carbon atoms, —O—, —S— and NR—, wherein R is a hydrogen atom or a monovalent hydrocarbon group having 1 to 20 carbon atoms, provided that the hetero atoms, oxygen atom, sulfur atom and nitrogen atom, are not adjacent to each other, a silyl group, a carbonyl group, a monovalent hydrocarbon group having 1 to 20 carbon atoms which may be substituted with a halogen atom, an amino group, a siloxy group, a halogen atom and a hydroxyl group. B is preferably an alkoxy group having 1 to 10 carbon atoms, more preferably a methoxy group.

The bonding order of the units represented by the formulas (I) and (II) is not limited. The siloxane units may be bonded randomly. The unit (I) and the unit (II) may be composed various structures.

In the polymer having the unit (I), p is an integer of 1 or more, such that the number average molecular weight of the

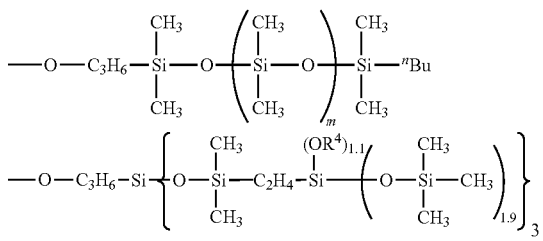

copolymer is 1,000 to 1,000,000 g/mol, preferably 3,000 to 100,000 g/mol, more preferably from 5,000 to 50,000 g/mol.

In the copolymer having the units (I) and (II), p is an integer of 1 or more, q is an integer of 1 or more, p+q is the number such that average molecular weight of the copolymer is 1,000 to 1,000,000 g/mol, preferably 3,000 to 100,000 g/mol, more preferably from 5,000 to 50,000 g/mol.

In the terminal structure (III), $R^7$ is an alkyl group having 1 to 4 carbon atoms, preferably a methyl group. $R^8$ and $R^9$ are, independently of each other, a hydrogen atom or an alkyl group having 1 to 4 carbon atoms, preferably a methyl group.

In the terminal structure (IV), $R^{10}$ is a hydrogen atom or a methyl group, and X is a structure as defined for A or B described above.

The present (meth)acrylic silicone graft (co)polymer is obtained by transfer polymerization of a monomer represented by the general formula (4) and a monomer represented by the general formula (5) in the presence of a compound represented by the following general formula (6) as an initiator.

The method for preparing the present (meth)acrylic silicone graft (co)polymer will be described below in detail.

The (meth)acrylic silicone graft (co) polymer having the unit (I) is obtained by transfer polymerization of a compound represented by the following general formula (4):

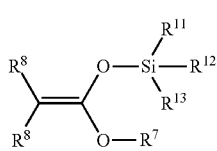
(4)

wherein $R^1$ and A are as defined above,
in the presence of a compound represented by the following general formula (6) as the initiator:

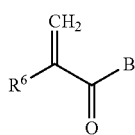
(6)

wherein $R^7$, $R^8$ and $R^9$ are as defined above, $R^{11}$, $R^{12}$ and $R^{13}$ are, independently of each other, an alkyl group having 1 to 4 carbon atoms.

The (meth)acrylic silicone graft (co)polymer having the units (I) and (II) is obtained by transfer polymerization of the compound represented by the general formula (4) and a compound represented by the following general formula (5)

(5)

wherein $R^6$ and B are as defined above
in the presence of a compound represented by the general formula (6).

The present method is characterized in that the (meth)acryl compound represented by the formula (4) or the (meth)acryl compounds represented by the formula (4) and the formula (5) are subjected to a group-polymerization using the (meth) acrylic compound represented by the formula (6) as an initiator. The copolymer obtained by this method has no unsaturated bond at any terminal. This copolymer is excellent in heat resistance and, therefore, thermal decomposition is less. Furthermore, according to the present method, it is possible to reduce the content of residual monomers as impurities in the copolymer and to provide a copolymer having a high purity.

The reaction mechanism for preparing the copolymer having the terminal structures (III) and (IV) by group-polymerizing the (meth) acrylic compound(s) in the presence of the initiator represented by the formula (6) will be, for example, explained as follows.

Group transfer polymerization

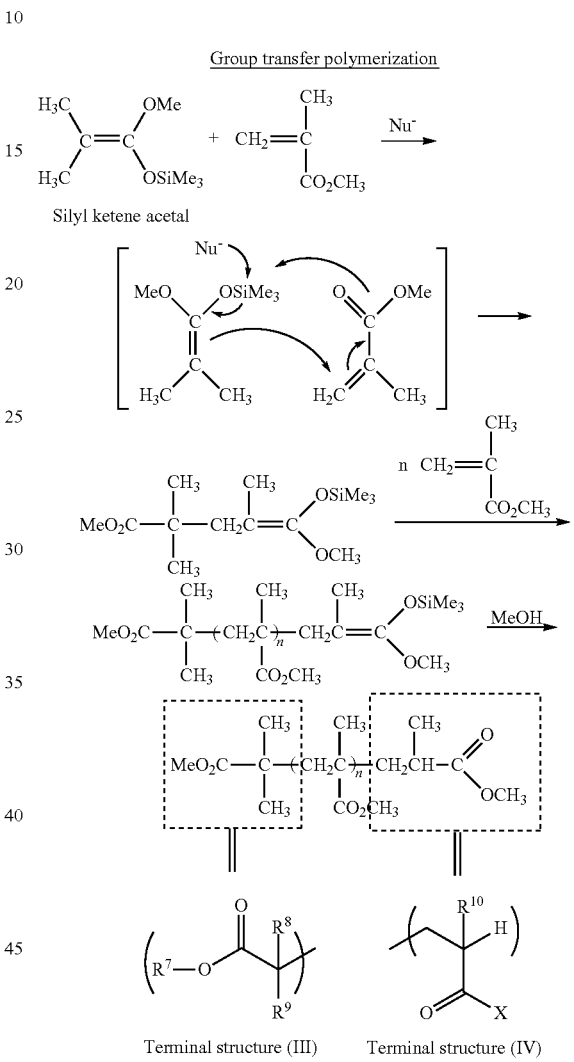

Terminal structure (III)    Terminal structure (IV)

Examples of the compound represented by the general formula (4) include the following compounds, but not limited thereto.

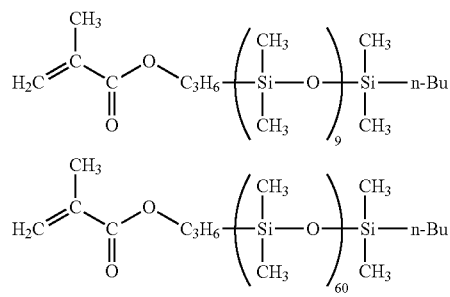

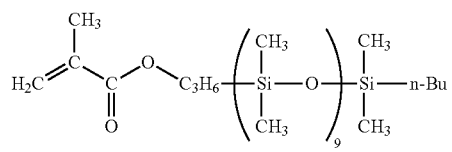
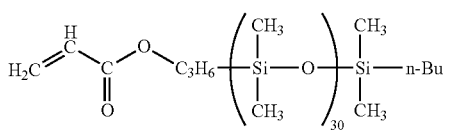
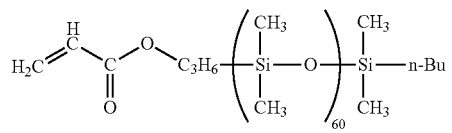
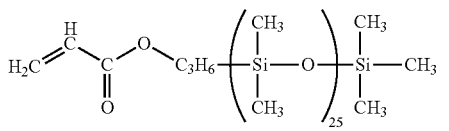
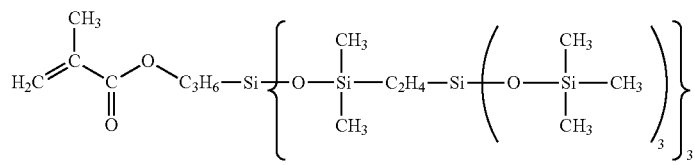
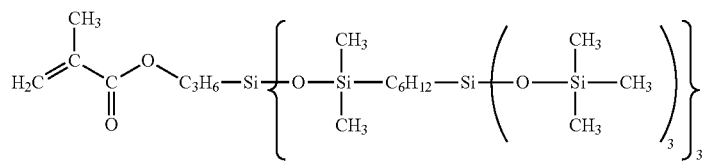
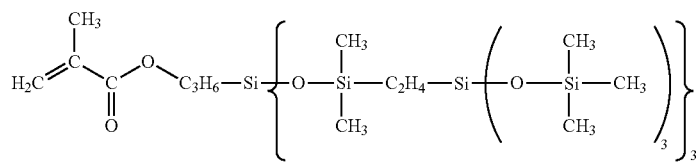
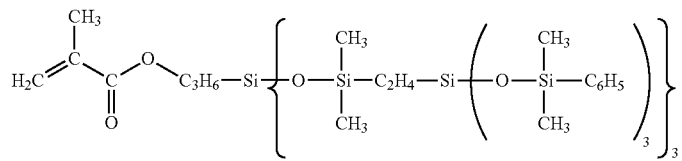
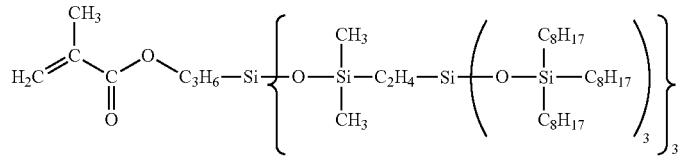
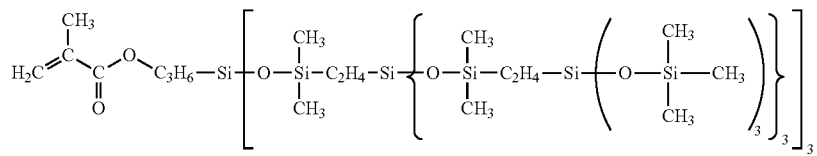
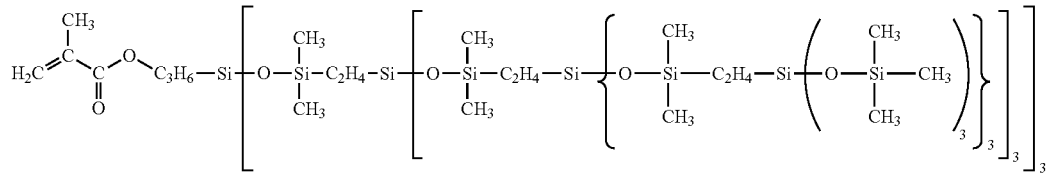
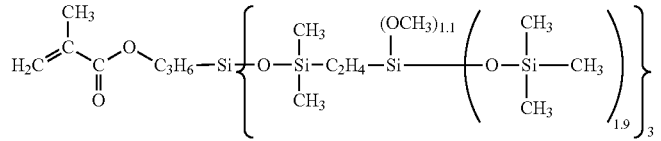
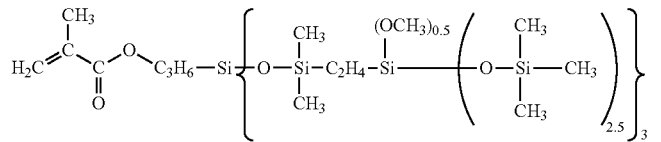

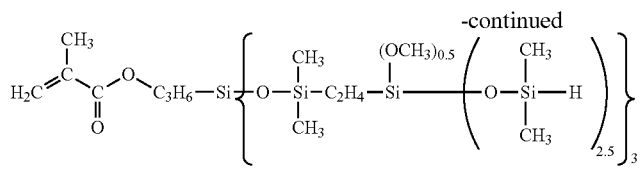

Examples of the compound represented by the general formula (5) include the following compounds.

Methyl(meth)acrylate, ethyl(meth)acrylate, n-butyl(meth)acrylate, tertiarybutyl(meth)acrylate, n-hexyl(meth)acrylate, isobutyl(meth)acrylate, isopentyl(meth)acrylate, lauryl(meth)acrylate, 2-ethylhexyl(meth)acrylate, stearyl(meth)acrylate, cyclohexyl(meth)acrylate, behenyl(meth)acrylate, isodecyl(meth)acrylate, 2-propylheptyl(meth)acrylate, 3,5,5-trimethyl-1-hexyl(meth)acrylate, nonanyl(meth)acrylate, 2-propylheptyl(meth)acrylate, 2-isopropyl-5-methylhexyl(meth)acrylate, tridecyl(meth)acrylate, heptadecyl(meth)acrylate, heneicosanyl(meth)acrylate, isobornyl(meth)acrylate, tetrahydrofurfuryl(meth)acrylate, di(ethyleneglycol)dimethylether(meth)acrylate, furfuryl(meth)acrylate, 2-butoxyethyl(meth)acrylate, 2-ethoxxyethyl(meth)acrylate, allyloxyethyl(meth)acrylate, 1-ethoxybutyl(meth)acrylate, tetrahydro-4H-pyranyl-2(meth)acrylate, ethyltriglycol(meth)acrylate, butyldiglycol(meth)acrylate, poly(propyleneglycol)dimethylether(meth)acrylate, poly(ethyleneglycol)alkylether(meth)acrylate, (meth)acrylamide, 4-(meth)acryloylmorpholine, N-tert-butyl(meth)acrylamide, N,N-dimethyl(meth)acrylamide, N,N-diethyl(meth)acrylamide, N-butoxymethyl(meth)acrylamide, N-[3-(dimethylamino)propyl](meth)acrylamide, N-dodecyl(meth)acrylamide and N-isopropyl(meth)acrylamide.

In the general formula (6), $R^7$ is an alkyl group having 1 to 4 carbon atoms, preferably 1 or 2 carbon atoms. $R^7$ is further preferably a methyl group. $R^8$ and $R^9$ are, independently of each other, a hydrogen atom or an alkyl group having 1 to 4 carbon atoms, preferably 1 or 2 carbon atom, further preferably a methyl group. $R^{11}$, $R^{12}$ and $R^{13}$ are, independently of each other, a hydrogen atom or an alkyl group having 1 to 4 carbon atoms, preferably 1 or 2 carbon atom, further preferably a methyl group.

Examples of the initiator represented by the general formula (6) include the following compounds, but not limited to these.

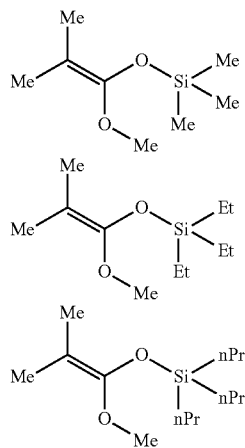

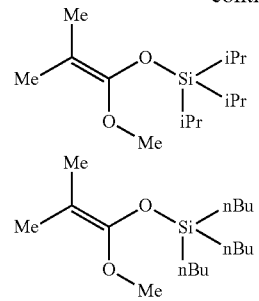

wherein Me is an abbreviation for a methyl group, Et is an abbreviation for an ethyl group, nPr is an abbreviation for a n-propyl group, iPr is an abbreviation for an isopropyl group, and nBu is an abbreviation for a n-butyl group.

Hereinafter, one example of the present preparation method will be described, but the present preparation method is not limited to the following method.

A solvent is added to a fully dried three-necked flask containing a catalyst. The initiator (6) is added to the flask and mixed and, then, monomers (4) and (5) are added dropwise to the mixture through a dripping funnel and stirred. The reaction solution may be cooled depending on the degree of heat generation and keep it at a proper temperature. Then, stirring is continued in order to proceed with the reaction of all of the monomer, a reaction terminator is added to stop the reaction. Then, unreacted monomers are distilled off under reduced pressure.

An order to add the group transfer polymerization catalyst, the solvent, the initiator and the monomers may be properly selected. For example, the catalyst may be added to a solution in which the monomer, the solvent and the initiator are mixed in advance.

All monomers used in the reaction are mixed in advance and added dropwise so as to obtain a random copolymer. Meanwhile, the monomers used in the reaction are alternately added in the reaction solution so as to obtain a block copolymer. For example, the monomer represented by the general formula (4) is first added dropwise to be reacted and, then, the monomer represented by the general formula (5) is added dropwise to the reaction mixture after confirming the completion of the reaction of the monomer (4) to thereby obtain an AB block copolymer. Therefore, various block copolymers such as ABAB block copolymer and ABC block copolymer can be prepared depending on the purpose.

An aprotic organic solvent may be used as a reaction solvent. For example, ethyl acetate, propionitrile, toluene, xylene, bromobenzene, dimethoxyethane, diethoxyethane, diethylether, tetramethylenesulfone, N,N-dimethylformamide, N,N-dimethylacetamide, N-methylpyrrolidone, anisole, 2-butoxyethoxytrimethylsilane, cellosolveacetate, crown ether, acetonitrile and tetrahydrofuran may be used. Preferred are dichloromethane, toluene, acetonitrile and tetrahydrofuran in view of a reaction efficiency. Tetrahydrofuran is further preferred.

The reaction temperature is a temperature of −100 degrees C. to 150 degrees C., preferably 0 to 50 degrees C., further preferably 10 to 30 degrees C.

The temperature of distilling off the monomer(s) is a temperature of 80 to 300 degrees C., preferably 100 to 200 degrees C., further preferably 120 to 180 degrees C. The pressure of stripping is at most 1 atm, preferably at most 0.1 atm, further preferably at most 0.001 atm.

The number average molecular weight (Mn) of the present (meth) acrylic silicone graft (co)polymer is 1,000 to 1,000,000 g/mol, preferably 3,000 to 100,000 g/mol, further preferably 5,000 to 50,000 g/mol. Polydispersity (Mw/Mn) is 1.00 to 3.00, preferably 1.05 to 2.00, further preferably 1.10 to 1.60.

Any catalyst selected from an anionic catalyst, a Lewis acid catalyst, or an organic molecular catalyst may be used, which are generally known as a catalyst for group transfer polymerization.

Anionic Catalyst

Examples of anionic catalyst include tris(dimethylamino)sulfoniumdifluorotrimethylsilicate, tris(dimethylamino)sulfoniumcyanide, tetraphenylarsoniumcyanide, tris(dimethylamino)sulfoniumazide, tetraethylammoniumazide, bis(dialkylaluminum)oxide, borontrifluorideetherate, an alkali metal fluoride, an alkali metal cyanide, an alkali metal azide, tris(dimethylamino)sulfoniumdifluorotriphenylstanate, tetrabutylammoniumfluoride, tetramethylammoniumfluoride, tetraethylammoniumcyanide, tetrabutylammoniumbenzoate, tetra butylammoniumbibenzoate, and tetrabutylammonium m-chlorobenzoate.

Lewis Acid

Examples of Lewis acid include zinc iodide, zinc bromide, zinc chloride, mono- and di-alkylaluminum halides, and dialkylaluminum oxides.

Organic Molecular Catalyst

Examples of the organic molecular catalyst include 1,3-diisopropyl-4,5-dimethylimidazole-2-ylidene, 1,3-diisopropylimidazole-2-ylidene, 1,3-di-tert-butylimidazole-2-ylidene, 1,8-diazabicyclo[5.4.0]-7-undecene, 2,8,9-trimethyl-2,5,8,9-tetraaza-1-phosphabicyclo[3.3.3]undecane, 2,8,9-triisobutyl-2,5,8,9-tetraaza-1-phosphabicyclo[3.3.3]undecane, 1-tert-butyl-2,2,4,4,4-pentakis (dimethylamino)-2$\lambda^5$,4$\lambda^5$-katenaji(phosphazene), 1-tert-butyl-4,4,4-tris(dimethylamino)-2,2-bis[tris(dimethylamino)-phosphoranylideneamino]-2$\lambda^5$,4$\lambda^5$-katenaji(phosphazene), tris(2,4,6-trimethoxyphenyl)phosphine, tris-(pentafluorophenyl)borane, trifluoromethanesulfonic acid triethylsilyl, triphenylcarbenium tetrakis(pentafluorophenyl)borate, trifluoromethane sulfonimide, and 1-[bis(trifluoromethanesulfonyl)methyl]-2,3,4,5,6-pentafluorobenzene.

As the reaction terminator, a compound capable of donating a proton is used. For example, methanol, isopropyl alcohol, n-butyl alcohol and water are used.

The present (meth) acrylic silicone graft (co)polymer (A) is used in various cosmetics. In particularly, it is suitable for all cosmetics which are applied to skin and hair. Preferably, the cosmetic of the present invention can be a cosmetic containing the copolymer (A) as a film agent and/or a thickener. The copolymer (A) has properties as a silicone polymer and simultaneously solves good compatibility with various oil agents and adhesion to skin or hair, so that it is suitable as a coating agent and/or a thickener. In the case where the present cosmetic is in the form of emulsion, the cosmetic may comprise the copolymer (A) as a surfactant. Since the copolymer (A) has a silicone moiety, a hydrophobic moiety, and a hydrophilic moiety, it can be used as an effective surfactant. Further, when the cosmetic contains powder (F), the cosmetic may comprise the copolymer (A) as the dispersant of the powder (F). The polyfunctional copolymer (A) can be suitably used as a dispersant for the powder (F). Examples of the cosmetics to be applied to the skin or hair include skin care cosmetics such as a milky lotion, a cream, a cleansing, a pack, an oil liquid, a massage fee, a beauty essence, a cleansing agent, a deodorant, a hand cream and a lip cream; makeup cosmetics such as a base powder, a white powder, a liquid foundation, an oil foundation, a blusher, an eye shadow, a mascara, an eyeliner, an eyebrow and a lipstick: hair cosmetics such as a shampoo, a rinse, a treatment and a setting agent; an antiperspirant; and UV protection cosmetics such as a sunscreen lotion and a sunscreen cream. The amount of the copolymer (A) contained in the cosmetic depends on the dosage form of the cosmetic, it may be used in the range of 0.5 to 99.0% by mass, preferably 1.0 to 50% by mass, based on the total mass of a cosmetic.

In addition to the (A) copolymer, the present cosmetic may comprise various components used in cosmetics, such as (B) an oil agent, (C) a ultraviolet absorbing, (D) water, (E) surfactant, (F) powder, (G) a compound having an alcoholic hydroxyl group in its molecular structure, (H) a water-soluble or water-swellable polymer, (I) a composition comprising a liquid oil agent and a crosslinked organopolysiloxane polymer having no hydrophilic group, (J) a composition comprising a liquid oil agent and a crosslinked organopolysiloxane polymer having a hydrophilic group, (K) a silicone resin, and/or (L) a silicone wax. Each component will be described below.

(B) Oil Agent

As described above, the present cosmetic may contain one or more oil agents. Any oil agent such as a solid oil, a semi-solid oil or a liquid oil which are used in ordinary cosmetics may be used. The present copolymer (A) has high compatibility with oil agents. Therefore, in the case when the present cosmetic contains the oil agent, the copolymer gives a less stickiness, a smooth extension, and a refreshing feeling of use to the cosmetic and provides a cosmetic which is rich in water repellency and has high safety, good feeling of use, excellent properties in use and sustainability.

Examples of the liquid oil agent include one or more silicone oils, polar oils such as hydrocarbon oils, higher fatty acids, ester oils and natural animal and vegetable oils; semi-synthetic oils and/or fluorine oils, and polar oil and silicone oil are preferred. Further, the (B) oil agent may also consist of one or more ester oils, natural animal and vegetable oils and one or more silicone oils. Even when the (B) oil agent consists of the relatively high polarity ester oil, a natural animal or vegetable oil and a relatively low polar silicone oil, the copolymer (A) contained in the present cosmetic has compatibility with any of these oils and, therefore, the cosmetic obtained gives less stickiness, smooth elongation and refreshing feeling of use and provides a cosmetic having rich in water repellency, high skin safety, good use feeling, properties in use and sustainability.

Examples of the silicone oils include low viscosity to high viscosity, linear or branched organopolysiloxanes such as such as dimethylpolysiloxane, caprylyl methicone, phenyl trimethicone, methylphenylpolysiloxane, methylhexyl polysiloxane, methylhydrogenpolysiloxane, and dimethylsiloxane/methylphenylsiloxane copolymer; cyclic organopolysiloxanes such as octamethylcyclotetrasiloxane, decamethylcyclopentasiloxane, dodecamethylcyclohexasiloxane, tetramethyltetrahydrogen cyclotetrasiloxane and tetramethyltetraphenylcyclotetrasiloxane; branched organopolysiloxanes such as tristrimethylsiloxymethylsilane and tetrakistrimethylsiloxysilane; amino-modified organopolysiloxane, silicone gums such as highly polymerized gum dimethylpolysiloxane, gummy amino-modified organopolysiloxane, gum-like dimethylsiloxane/methylphenylsiloxane copolymer; a cyclic siloxane solution of silicone gum or rubber, trimethylsiloxy silicic acid, a cyclic organopolysiloxane solution of trimethylsiloxysilicic acid, a higher alkoxy-modified organopolysiloxane such as stearoxy silicone; a higher fatty acid-modified organopolysiloxane, an alkyl-modified organopolysiloxane, a long-chain alkyl-modified organopolysiloxane, a fluorine-modified organopolysiloxane, silicone resin and a solution of silicone resin.

Examples of hydrocarbon oils include linear, branched and volatile hydrocarbon oils such as ozokerite, α-olefin oligomer, light isoparaffin, isododecane, light liquid isoparaffin, squalane, synthetic squalane, vegetable squalane, squalene, ceresin, paraffin, paraffin wax, polyethylene wax, polyethylene-polypropylene wax, (ethylene/propylene/styrene) copolymer, (butylene/propylene/styrene) copolymer, liquid paraffin, liquid isoparaffin, pristane, polyisobutylene, hydrogenated polyisobutene, microcrystalline wax and vaseline.

Examples of the higher fatty acid include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid. Examples of higher alcohols include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyl tetradecynol, cholesterol, phytosterol, POE cholesterol ether, monostearyl glycerin ether (batyl alcohol) and monooleyl glyceryl ether (serachyl alcohol).

Examples of the ester oil include diisobutyl adipate, 2-hexyldecyl adipate, di-2-heptylundecyl adipate, N-alkyl glycol monoisostearate, isocetyl isostearate, trimethylolpropane triisostearate, di-2-ethyl hexanoic acid ethylene glycol, cetyl 2-ethylhexanoate, tri-2-ethylhexanoate trimethylolpropane, pentaerythritol tetra-2-ethylhexanoate, cetyl octanoate, octyldodecy gum ester, oleyl oleate, octyl oleate dodecyl, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyl octanoate, ethyl laurate, hexyl laurate, N-lauroyl-L-glutamic acid 2-octyldodecyl ester, lauroyl sarcosine isopropyl ester and diisostearyl malate. Examples of the glyceride oil include acetoglyceryl, glyceryl triisooctanoate, glyceryl triisostearate, glyceryl triisopalmitate, glyceryl monostearate, glyceryl di-2-heptylundecanoate, glyceryl trimyristate and diglyceryl isostearate/myristate.

Examples of natural animal and vegetable oils and semi-synthetic oils include avocado oil, linseed oil, almond oil, Ibota wax, perilla oil, olive oil, cacao butter, kapok wax, kaya oil, carnauba wax, liver oil, candelilla wax, purified candelilla wax, beef tallow, beef leg fat, beef bone fat, hardened beef tallow, apricot kernel oil, spermaceti, hardened oil, wheat germ oil, sesame oil, rice germ oil, rice bran oil, sugar cane wax, sasanqua oil, safflower oil, shea butter, sinagiri oil, cinnamon oil, Jojobarou, squalane, squalene, shellac wax, turtle oil, soybean oil, tea seed oil, camellia oil, evening primrose oil, corn oil, lard, rapeseed oil, Japanese tung oil, nucca wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba oil, macadamia nut oil, beeswax, mink oil, meadowfoam oil, cotton seed oil, cotton wax, japan wax, japan kernel wax, montan wax, coconut oil, hardened coconut oil, tri-coconut oil fatty acid glyceride, mutton tallow, peanut oil, lanolin, liquid lanolin, reduced lanolin, lanolin alcohol, hard lanolin, lanolin acetate, lanolin alcohol acetate, lanolin fatty acid isopropyl, POE lanolin alcohol ether, POE lanolin alcohol acetate, lanolin fatty acid polyethylene glycol, POE hydrogenated lanolin alcohol ether and Egg yolk oil. POE means polyoxyethylene.

Examples of the fluorine-based oil agent include perfluoropolyether, perfluorodecalin and perfluorooctane.

The amount of the (B) oil agent in the present cosmetic may depend on the cosmetic agent system, but is preferably in the range of 1 to 98% by mass, preferably 1 to 50% by mass, based on the total mass of cosmetic.

(C) UV Absorbing Component

The present cosmetic may further contain one or more ultraviolet absorbing components. The present cosmetic comprising the ultraviolet absorbing component has excellent properties in use and sustainability and absorbs ultraviolet rays. The ultraviolet absorbing component includes an ultraviolet absorber and an ultraviolet scattering agent. Examples of the ultraviolet absorber include a benzoic acid type ultraviolet absorber such as paraaminobenzoic acid, an anthranilic acid type ultraviolet absorber such as methyl anthranilate, a salicylic acid type ultraviolet absorber such as methyl salicylate, a cinnamon type ultraviolet absorber such as octylparamethoxycinnamate, a benzophenone type ultraviolet absorber such as 2,4-dihydroxybenzophenone, a urocanic acid type ultraviolet absorber such as ethyl urocanate, and dibenzoyl methane type ultraviolet absorber such as 4-t-butyl-4'-methoxy-dibenzoylmethane. Further, the aforementioned silicone derivative having a ultraviolet absorbing functional group may also be used. Examples of the ultraviolet absorbing/scattering agent include particles which absorb and scatter ultraviolet rays, such as fine particle titanium oxide, fine particulate iron-containing titanium oxide, fine particulate zinc oxide, fine particulate cerium oxide, and complexes thereof. Among these, cinnamic acid type ultraviolet absorbers, dibenzoylmethane type ultraviolet absorbers, titanium oxide and zinc oxide are preferable.

(D) Water

Water may be contained in the present cosmetic depending on its purpose. On account of blending water according to the purpose of use, the cosmetics has better properties in use. The blending amount of water is preferably in the range of 95% by mass or less based on the total mass of the cosmetic.

(E) Surfactant

The present cosmetic may further comprise one or more surfactants. On account of blending surfactants according to the purpose of use, the cosmetic has better properties in use. Any surfactant used in ordinary cosmetics such as anionic, cationic, nonionic and amphoteric surfactants may be used and is not particularly limited.

Examples of the anionic surfactant include fatty acid soaps such as sodium stearate and triethanolamine palmitate, alkyl ether carboxylic acids and salts thereof, condensates of amino acids and fatty acids, alkanesulfonates, alkenesulfonates, sulfonate fatty acid esters, sulfonic acid salts of fatty acid amides, formalin condensation sulfonates, alkyl sulfates, secondary higher alcohol sulfuric ester salts, alkyl and allyl ether sulfate, sulfuric ester salts of fatty acid esters, sulfate ester salts of fatty acid alkylolamide, sulfate ester salts of sulfated caster oil, alkyl phosphate, ether phosphate, alkyl allyl ether phosphate, amide phosphate, N-acyl lactate, N-acyl sarcosine salt and N-acylamino acid type activator. Examples of the cationic surfactant include alkylamine salt, amine salts of polyamine and amino alcohol fatty acid derivative, alkyl quaternary ammonium salt, aromatic quaternary ammonium salt, pyridium salt and imidazolium salt.

Examples of the nonionic surfactant include sorbitan fatty acid ester, glycerin fatty acid ester, polyglycerin fatty acid ester, propylene glycol fatty acid ester, polyethylene glycol fatty acid ester, sucrose fatty acid ester, methyl glucoside fatty acid ester, alkyl polyglucoside, polyoxyethylene alkyl ether, polyoxypropylene alkyl ether, polyoxyethylene alkyl phenyl ether, polyoxyethylene fatty acid ester, polyoxyethylene sorbitan fatty acid ester, polyoxyethylene sorbitol fatty acid ester, polyoxyethylene glycerin fatty acid ester, polyoxyethylene propylene glycol fatty acid ester, polyoxyethylene castor oil, polyoxyethylene hardened castor oil, polyoxyethylene phytosterol ether, polyoxyethylene phytosterol ether, polyoxyethylene cholestanol ether, polyoxyethylene cholesterol ether, linear or branched polyoxyalkylene-modified organopolysiloxane, a linear or branched polyoxyalkylene/alkyl co-modified organopolysiloxane, a linear or branched polyglycerin-modified organopolysiloxane, a linear or branched polyglycerin/alkyl co-modified organopolysiloxane, an alkanol amide, a sugar ether and a sugar amide.

Examples of the amphoteric surfactant include betaine, aminocarboxylic acid salt, imidazoline derivative and amidoamine type.

Among these surfactants, a linear or branched organopolysiloxane having a polyoxyethylene chain in the molecule, a linear or branched organopolysiloxane having a polyglycerol chain in the molecule, or an alkyl co-modified organopolysiloxane thereof is preferable. Examples of commercially available products include, but are not limited to these, KF-6011, KF-6011P, KF-6043, KF-6012, KF-6013, KF-6015, KF-6016, KF-6017, KF-6028, KF-6028P, KF-6038, KF-6100, KF-6104, KF-6105 and KF-6106, all manufactured by Shin-Etsu Chemical Co., Ltd. Further, a surfactant having an HLB of 2 to 10 is preferable, and the amount thereof is preferably 0.1 to 20% by mass, more preferably 0.2 to 10% by mass, based on the total mass of a cosmetic.

(F) Powder

The cosmetic of the present invention may further contain one or two or more kinds of powders. Any powder used in ordinary cosmetics may be used, which may have any shape such as spherical, needle-like and plate-like, any particle size such as fumed, fine particles and pigment grade and any particle structure such as porous and nonporous. For example, inorganic powders, organic powders, surfactant metal salt powders, colored pigments, pearl pigments, tar dyes, metal powder pigments, natural pigments and dyes are used.

Examples of the inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, mica, biotite, lithia mica, silicic acid, anhydrous silicic acid, aluminum silicate, magnesium silicate, magnesium aluminum silicate, calcium silicate, barium silicate, strontium silicate, metal tungstate salt, hydroxyapatite, vermiculite, hygilite, bentonite, montmorillonite, hectorite, zeolite, ceramics powder, calcium dihydrogen phosphate, alumina, aluminum hydroxide, boron nitride, boron nitride, silica, and silylated silica.

Examples of the organic powder include polyamide powder, polyacrylic acid-acrylic acid ester powder, polyester powder, polyethylene powder, polypropylene powder, polystyrene powder, polyurethane, benzoguanamine powder, polymethylbenzoguanamine powder, tetrafluoroethylene powder, polymethyl methacrylate powder, cellulose, silk powder, nylon powder, 12-nylon, 6-nylon, crosslinked spherical dimethylpolysiloxane fine powder having a crosslinked structure of dimethylpolysiloxane, crosslinked spherical polymethylsilsesquioxane fine powder, crosslinked spherical organopolysiloxane rubber fine powder coated with polymethylsilsesquioxane particles, hydrophobized silica, styrene/acrylic acid copolymer, divinylbene/styrene copolymer, vinyl resin, urea resin, phenol resin, fluorine resin, silicone resin, acrylic resin, melamine resin, epoxy resin, polycarbonate resin, microcrystalline fiber powder, starch powder, fatty acid starch derivative powder and lauroyl lysine.

Examples of the surfactant metal salt powder (metal soap) include zinc undecylenate, aluminum isostearate, zinc stearate, aluminum stearate, calcium stearate, magnesium stearate, zinc myristate, magnesium myristate, zinc cetyl phosphate, calcium cetyl phosphate, sodium zinc cetyl phosphate, zinc palmitate, aluminum palmitate and zinc laurate.

Examples of the colored pigments include inorganic red pigments such as iron oxide, iron hydroxide and iron titanate; inorganic brown pigments such as γ-iron oxide; inorganic yellow pigments such as yellow iron oxide and loess; inorganic black pigments such as black iron oxide and carbon black; inorganic violet pigments such as manganese violet and cobalt violet; inorganic green pigments such as chromium hydroxide, chromium oxide, cobalt oxide and cobalt titanate; inorganic blue pigments such as prussian blue and ultramarine blue; lake pigment of tar dyes, lake pigment of natural pigment and a synthetic resin powder obtained by combining these powders.

Examples of the pearl pigment include titanium oxide-coated mica, titanium oxide-coated mica, bismuth oxychloride, titanium oxide-coated bismuth oxychloride, titanium oxide-coated talc, fish scale foil and titanium oxide-coated colored mica. Examples of the metal powder pigments include aluminum powder, copper powder and stainless steel powder.

Examples of the tar pigment include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Examples of the natural pigments include powders selected from carminic acid, laccaic acid, carthamin, brazilin and crocin.

Among these powders, crosslinked spherical dimethyipolysiloxane fine powder having at least a partially crosslinked dimethylpolysiloxane structure, cross-linking type spherical polymethylsilsesquioxane fine powder, fine powder of a crosslinked spherical polysiloxane rubber with polymethylsilsesquioxane particles, whose surface is coated with polymethylsilsesquioxane particles, or a hydrophobized silica is preferable in the present invention. A powder having a fluorine group and a coloring agent may be also used. Examples of commercially available products include KMP-590, KSP-100, KSP-101, KSP-102, KSP-105 and KSP-300, all manufactured by Shin-Etsu Chemical Co., Ltd.

The complex powder or the powder treated with general oil, silicone oil, fluorine compound or surfactant may be used, as long as the effect of the present invention is not hindered. For example, powder may be surface treated in advance by a fluorine compound treatment, a silicone resin treatment, a pendant treatment, a silane coupling agent treatment, a titanium coupling agent treatment, an oil treatment, an N-acylated lysine treatment, a polyacrylic acid treatment, a metal soap treatment, an amino acid treatment, inorganic compound treatment, plasma treatment or mechanochemical treatment. The powder may be one or two or more kinds as needed. The amount of the powder is preferably 99% by mass or more, based on the total mass of cosmetic. In particular, in the case of a powder cosmetic, the amount is preferably 80 to 99% by mass, based on the total mass of cosmetic.

(G) A Compound Having an Alcoholic Hydroxyl Group in its Molecular Structure

The present cosmetic may further comprise one or more compounds having an alcoholic hydroxyl group in the molecular structure. The alcohol compound having 12 or more carbon atoms for constituting the monomer unit (II) of the aforesaid copolymer is excluded from the (G) compound having an alcoholic hydroxyl group. Examples of such compounds include lower alcohols such as ethanol and isopropanol; sugar alcohols such as sorbitol and maltose; sterols such as cholesterol, sitosterol, phytosterol and lanosterol; and polyhydric alcohols such as butylene glycol, propylene glycol, dibutylene glycol and pentylene glycol. The water-soluble monohydric alcohols and the water-soluble polyhydric alcohols are generally used. The amount of the compound having an alcoholic hydroxyl group in the molecular structure is preferably 98% by mass or less, based on the total mass of the cosmetics.

(H) Water-Soluble or Water-Swellable Polymer

The present cosmetic may further comprise one or two or more (H) water-soluble or water-swellable polymers. Examples of these water-soluble or water-swellable polymers include plant-based polymers such as gum arabic, tragacanth, galactan, carob gum, guar gum, karaya gum, carrageenan, pectin, agar, quince seed (quince seed), starch (rice, corn, potato, wheat), alga colloid, trant gum and locust bean gum; microbial polymers such as xanthan gum, dextran, succinoglucan and pullulan; animal polymers such as collagen, casein, albumin and gelatin; starch polymers such as carboxymethyl starch and methyl hydroxypropyl starch; methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, cellulose polymers of powdered cellulose; alginate polymers such as sodium alginate and propylene glycol esters of alginic acid; vinyl polymers such as polyvinyl methyl ether and carboxy vinyl polymer; polyoxyethylene based polymers, polyoxyethylene polyoxypropylene copolymer, acrylic polymers such as sodium polyacrylate, polyethyl acrylate, polyacrylamide, acryloyl dimethyl taurine salt copolymer; synthetic water-soluble polymers such as polyethylene imine and cationic polymers; inorganic water-soluble polymers such as bentonite, magnesium aluminum silicate, montmorillonite, beidellite, nontronite, saponite, hectorite and anhydrous silicic acid. Furthermore, these water-soluble polymers also include film forming agents such as polyvinyl alcohol and polyvinyl pyrrolidone. The amount of the water-soluble or water-swellable polymer (H) is preferably 25% by mass or less, based on the total mass of the cosmetic.

(I) Composition Comprising a Liquid Oil Agent and a Crosslinked Organopolysiloxane Polymer Without Hydrophilic Group The present cosmetic may further comprise a (I) composition comprising a liquid oil agent and one or more crosslinked organopolysiloxane polymer without hydrophilic group. The crosslinked organopolysiloxane polymer is obtained by reacting an alkylhydrogenpolysiloxane with a crosslinking agent having a reactive vinylic unsaturated group at the molecular chain terminal. Examples of the alkyl hydrogen polysiloxane include methyl hydrogen polysiloxane having a linear or partially branched unit and methyl hydrogen polysiloxane grafted with an alkyl chain having 6 to 20 carbon atoms. On average, two or more hydrogen atoms bonded to silicon atoms are required in the molecule. Examples of the crosslinking agent include those having two or more vinylic reactive moieties in the molecule, such as methylvinylpolysiloxane and α,ω-alkenyldiene. Examples of these are the compositions described in Japanese Patent No. 192571, Japanese Patent No. 1932769, WO03-24413 and Japanese Patent Application Laid-Open No. 2009-185296. For example, the crosslinked methylpolysiloxane is swelled with a low viscosity silicone having a viscosity more than its own weight, such as 0.65 $mm^2$/sec to 100.0 $mm^2$/sec at 25 degrees C., a hydrocarbon oil such as liquid paraffin, squalane and isododecane, glyceride oil such as trioctanoyin, and ester oil. The commercially available products as these crosslinked organopolysiloxanes are not particularly limited, but KSG-15, KSG-16, KSG-18, KSG-1610 and USG-103 which are made into paste form with silicone oil, USG-106, KSG-41, KSG-42, KSG-43, KSG-44, KSG-810 which are made into a paste with hydrocarbon oil or triglyceride oil (all manufactured by Shin-Etsu Chemical Co., Ltd.). The amount of the composition (I) is preferably 0.1 to 50% by mass, more preferably 1 to 30% by mass, based on the total mass of the cosmetic.

(J) Composition Comprising a Crosslinked Organopolysiloxane Polymer Having One or More Hydrophilic Groups and a Liquid Oil Agent The present cosmetic may further comprise a composition comprising a crosslinked organopolysiloxane polymer having one or more hydrophilic groups and a liquid oil agent. The hydrophilic group is preferably a polyether group or a polyglycerol group. The crosslinked organopolysiloxane having the polyether group and/or a polyglycerol group is obtained by reacting with an alkyl hydrogen polysiloxane and a crosslinking agent having a reactive vinylic unsaturated group in the molecular chain terminal. For instance, methylhydrogen polysiloxane grafted with polyoxyethylene chain and methylhydrogen polysiloxane grafted with polyglycerol chain are used as the alkyl hydrogen polysiloxane. Two or more, on average, hydrogen atoms bonded to the silicon atom are required. For example, the crosslinked organopolysiloxane is swelled with a low viscosity silicone having a viscosity more than its own weight, such as 0.65 $mm^2$/sec to 100.0 $mm^2$/sec at 25 degrees C., a hydrocarbon oil such as liquid paraffin, squalane and isododecane, glyceride oil such as trioctanoyin, and ester oil. The crosslinking agent may be those having two or more vinylic reactive sites in the molecule, such as methylvinyl polysiloxane, α,ω-alkenyldiene, glyceroltriallyl ether, polyoxyalkynylated glycerol triallyl ether, trimethylolpropane triallyl ether, and polyoxyalkynylated trimethylolpropane triallyl ether. The crosslinked products obtained by reacting these has at least one hydrophilic group. As the composition (J), those described in Japanese Patent No. 2631772, Japanese Patent Application Laid-Open No. 9-136813, Japanese Patent Application Laid-Open No. 2001-342255, WO03/20828 and Japanese Patent Application Laid-Open No. 2009-185296 are preferable. The commercially available products as these crosslinked organopolysiloxanes are not particularly limited, but KSG-210, KSG-240 and KSG-710 which are in a paste form with silicone oil, KSG-310, KSG-320, KSG-330, KSG-340, KSG-820, KSG-830 and KSG-840 which are in a paste form with hydrocarbon oil or triglyceride oil, all manufactured by Shin-Etsu Chemical Co., Ltd. The amount of the composition (J) is preferably 0.1 to 50% by mass, more preferably from 0.1 to 30% by mass, based on the total mass of the cosmetic.

(K) Silicone Resin

The present cosmetic may further comprise one or more (K) silicone resins. The silicone resin is preferably selected from a silicone network compound having $SiO_2$ unit and/or $RSiO_{1.5}$ unit, wherein R is an alkyl group, a linear acrylic/silicone graft, and a block copolymer thereof. The linear acrylic/silicone graft and the aforesaid copolymer may have at least one selected from pyrrolidone moiety, long chain alkyl moiety, polyoxyalkylene moiety, and fluoroalkyl moiety and anionic moiety such as carboxylic acid. Examples of commercially available products include, but are not limited to these, KP-541, KP-543, KP-545, KP-549, KP-550, KP-571, KP-575 and KP-581, which are dissolved in a silicone oil, a hydrocarbon oil or an alcohol, all manufactured by Shin-Etsu Chemical Co., Ltd.

The silicone network compound is preferably a silicone network compound represented by MQ, MDQ, MT, MDT or MDTQ. M, D, T and Q respectively represent $R_3SiO_{0.5}$ unit, $R_2SiO$ unit, $RSiO_{1.5}$ unit and $SiO_2$ unit. The silicone network compound may have at least one selected from a pyrrolidone moiety, a long chain alkyl moiety, a polyoxyalkylene moiety, a fluoroalkyl moiety and an amino moiety in the molecule. Examples of commercially available products include, but are not limited to these, KF-7312J, KF-7312 K, KF-7312T, all manufactured by Shin-Etsu Chemical Co., Ltd.

The silicone resin may be dissolved in low viscosity silicone oil, volatile silicone oil, or other solvent. The amount of the diluted silicone resin is such an amount that the amount of the silicone resin is preferably 0.1 to 20% by mass, more preferably 1 to 10% by mass, based on the total amount of the cosmetic.

(L) Silicone Wax

The present cosmetic may comprise (L) silicone wax depending on its purpose. The silicone wax is preferably a polylactone-modified polysiloxane in which a polylactone obtained as a ring-opening polymer of a 5-membered or more lactone compound is bonded. Alternatively, the silicone wax may be an acrylic modified polysiloxane having at least one functional group selected from a pyrrolidone group, a long chain alkyl group, a polyoxyalkylene group, a fluoroalkyl group, and an anion group such as carboxylic acid. Examples of commercially available wax, which has a long chain alkyl group, include KP-561P and KP-562P, all manufactured by Shin-Etsu Chemical Co., Ltd.

Alternatively, the silicone wax is preferably a silicone-modified olefin wax obtained by addition reaction of an olefin wax with an organohydrogenpolysiloxane having one or more SiH bonds in one molecule. The olefin wax is one obtained by copolymerizing ethylene and at least one diene or one obtained by copolymerizing ethylene, at least one olefin selected from α-olefins having 3 to 12 carbon atoms and at least one diene. The diene is preferably vinyl norbornene.

Regardless of any silicone wax is selected, the amount is preferably 0.1 to 20% by weight, more preferably 1 to 10% by weight, based on the total amount of the cosmetic.

Other Components

Furthermore, the present cosmetic may further comprise, within the range not hindering the effect of the present invention, ingredients usually used in cosmetics such as oil-soluble gelling agents, organomodified clay minerals, resins, antiperspirants, humectants, antiseptics, anti-microbial agents, perfumes, salts, antioxidants, pH adjusting agents, chelating agents, refreshing agents, anti-inflammatory agents, ingredients for skin (whitening agents, cell activating agents, rough skin improving agents, blood circulation promoting agents, skin astringent agents and anti-seborrheic agents), vitamins, amino acids, nucleic acids, hormones, inclusion compounds, and hair fixation agents.

Examples of the oil-soluble gelling agent include metal soaps such as aluminum stearate, magnesium stearate and zinc myristate; amino acid derivatives such as N-lauroyl-L-glutamic acid, α,γ-di-n-butylamine; dextrin fatty acid esters such as dextrin palmitate ester, dextrin stearate ester, dextrin 2-ethylhexanoate palmitate ester; sucrose fatty acid esters such as sucrose palmitate and sucrose stearate; fructooligosaccharide fatty acid esters such as fructooligosaccharide stearate ester and fructooligosaccharide 2-ethylhexanoate ester; benzylidene derivatives of sorbitol such as monobenzylidene sorbitol and dibenzylidenesorbitol; and organically modified clay minerals such as dimethylbenzyldodecyl ammonium montmorillonite clay and dimethyl dioctadecyl ammonium montmorillonite clay.

Examples of the antiperspirant include aluminum chlorohydrate, aluminum chloride, aluminum sesquichlorohydrate, zirconyl hydroxychloride, aluminum zirconium hydroxychloride and aluminum zirconium glycine complex.

Examples of the humectant include glycerin, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carboxylate, polyoxyethylene methyl glucoside and polyoxypropylene methyl glucoside.

Examples of the antimicrobial preservative include paraoxybenzoic acid alkyl ester, benzoic acid, sodium benzoate, sorbic acid, potassium sorbate and phenoxyethanol. Examples of the antibacterial agent include benzoic acid, salicylic acid, carbolic acid, sorbic acid, paraoxybenzoic acid alkyl esters, parachloromethacresol, hexachlorophene, benzalkonium chloride, chlorhexidine chloride, trichlorocarbanilide, photosensitizers and phenoxyethanol.

Examples of the salts include inorganic salts, organic acid salts, amine salts and amino acid salts. Examples of the inorganic salt include sodium salt, potassium salt, magnesium salt, calcium salt, aluminum salt, zirconium salt or zinc salt of an inorganic acid such as hydrochloric acid, sulfuric acid, carbonic acid and nitric acid. Examples of the organic acid salt include salts of organic acids such as acetic acid, dehydroacetic acid, citric acid, malic acid, succinic acid, ascorbic acid and stearic acid. Examples of the amine salts and amino acid salts include salts of amines such as triethanolamine and amino acids such as glutamic acid. Additionally, salts of hyaluronic acid or chondroitin sulfate, aluminum zirconium glycine complex, and acid-alkali neutralization salts used in cosmetic formulations can also be used.

Examples of the antioxidant include tocopherol, butylhydroxyanisole, dibutylhydroxytoluene and phytic acid. Examples of the pH adjuster include lactic acid, citric acid, glycolic acid, succinic acid, tartaric acid, dl-malic acid, potassium carbonate, sodium hydrogencarbonate and ammonium hydrogen carbonate. Examples of chelating agents include alanine, edetate sodium salt, sodium poly-phosphate, sodium metaphosphate, and phosphoric acid. Examples of refreshing agents include L-menthol and camphor. Examples of anti-inflammatory agents include one or more oxidation preservatives selected from allantoin, glycyrrhizic acid and a salt thereof, glycyrrhetinic acid, stearyl glycyrrhetinate, tranexamic acid and azulene.

Examples of the skin-beautifying component include one or more natural skin ingredients selected from whitening agents such as placenta extract, arbutin, glutathione and Yukitoshita extract; cell activators such as royal jelly, photosensitizer, cholesterol derivative and bovine blood extract; rough skin improver; blood circulation promoter such as nonyl acid varenylamide, nicotinic acid benzyl ester, nicotinic acid beta-butoxyethyl ester, capsaicin, zingerone, cantharides tincture, ichthammol, caffeine, tannic acid, alpha-borneol, tocopherol nicotinate, inositol hexanicotinate, cyclandelate, cinnarizine, trazolin, acetylcholine, verapamil, cepharanthin and γ-oryzanol; skin astringents such as zinc oxide and tannic acid; and antiseborrheic agents such as sulfur and thiantrol.

Examples of the vitamins include vitamin A such as vitamin A oil, retinol, acetic acid retinal and retinol palmitate; vitamin B2 such as riboflavin, riboflavin butyrate and flavin adenine nucleotide; vitamin B6 such as pyridoxine hydrochloride, pyridoxine dioctanoate and pyridoxine tripalmitate; vitamin B such as vitamin B12 and its derivatives and vitamin B15 and its derivatives; vitamin C such as L-ascorbic acid, L-ascorbic acid dipalmitate, sodium L-ascorbate-2-sulfate, L-ascorbylphosphate diester dipotassium; vitamin D such as ergocalciferol and cholecalciferol; vitamin E such as alpha-tocopherol, beta-tocopherol, gamma-tocopherol, acetic acid dl-alpha-tocopherol, nicotinic acid dl-alpha-tocopherol, succinate dl-alpha-tocopherol; vitamin H, vitamin P, nicotinic acids such as nicotinic acid, benzyl nicotinate and nicotinic acid amide; pantothenic acids such as calcium pantothenate, D-pantothenyl alcohol, pantothenyl ethyl ether and acetylpanthothenyl ethyl ether; and biotin.

Examples of the amino acids include glycine, valine, leucine, isoleucine, serine, threonine, phenylalanine, arginine, lysine, aspartic acid, glutamic acid, cystine, cysteine, methionine and tryptophan. Examples of the Nucleic acid include deoxyribonucleic acid. Examples of the hormone include estradiol and ethenyl estradiol.

Examples of the polymer compound as hair fixation include amphoteric, anionic, cationic, or nonionic polymer compounds such as polyvinyl pyrrolidone polymers such as polyvinyl pyrrolidone, vinyl pyrrolidone/vinyl acetate copolymer; acidic vinyl ether type polymer compounds such as methyl vinyl ether/maleic anhydride alkyl half ester copolymer; acidic polyvinylacetate type polymers such as vinyl acetate/crotonic acid copolymer; acidic acrylic polymer compounds such as (meth)acrylic acid/alkyl(meth)acrylate copolymer and (meth)acrylic acid/alkyl(meth)acrylate/alkylacrylamide copolymer; amphoteric acrylic polymer compounds such as N-methacryloylethyl-N,N-dimethylammonium/α-N-methylcarboxybetaine/alkyl(meth)acrylate copolymer, and hydroxypropyl(meth)acrylate/butylaminoethyl methacrylate/acrylic acid octylamide copolymer. Further, naturally occurring polymer compounds such as cellulose or derivatives thereof, keratin and collagen or derivatives thereof are preferably used.

Examples of the present cosmetic include skin care cosmetics such as milky lotions, creams, cleansing, packs, massage fees, essence liquids, cosmetic oils, detergents, deodorants, hand creams, lip creams and wrinkles makeup cosmetic; makeup cosmetics such as makeup bases, concealers, white powders, liquid foundations, oil foundations, blushers, eye shadows, mascaras, eyeliners, eyebrows, and lipsticks; hair cosmetics such as shampoos, rinses, treatments and setting agents; UV protection cosmetics such as antiperspirants, sunscreen oils, sunscreen milky lotions and sunscreen creams.

Any shape of the cosmetic such as liquid, emulsion, cream, solid, paste, gel, powder, press, multilayer, mousse, spray or stick may be selected.

Further, any form of the cosmetics may be selected, such as aqueous, oily, water-in-oil emulsion, oil-in-water emulsion, nonaqueous emulsion, or multi-emulsion such as W/O/W or O/W/O.

EXAMPLES

The present invention will be explained below in further detail with reference to a series of the Examples and the Comparative Examples, though the present invention is in no way limited by these Examples.

In the following descriptions, unless otherwised stated, the term "%" means % by mass of each component, based on total mass of a composition. The viscosity was determined at 25 degrees C. GPC was determined with HLC-8220 GPC, ex TOSO Co. Ltd. GC-MS was determined with 7697 A headspace sampler, 7890 B GC system and 5977 AMSD (all manufactured by Agilent Technologies). NMR was determined with AVANCE III 400, ex BROKER Corporation.

Example 1

Figure 2:
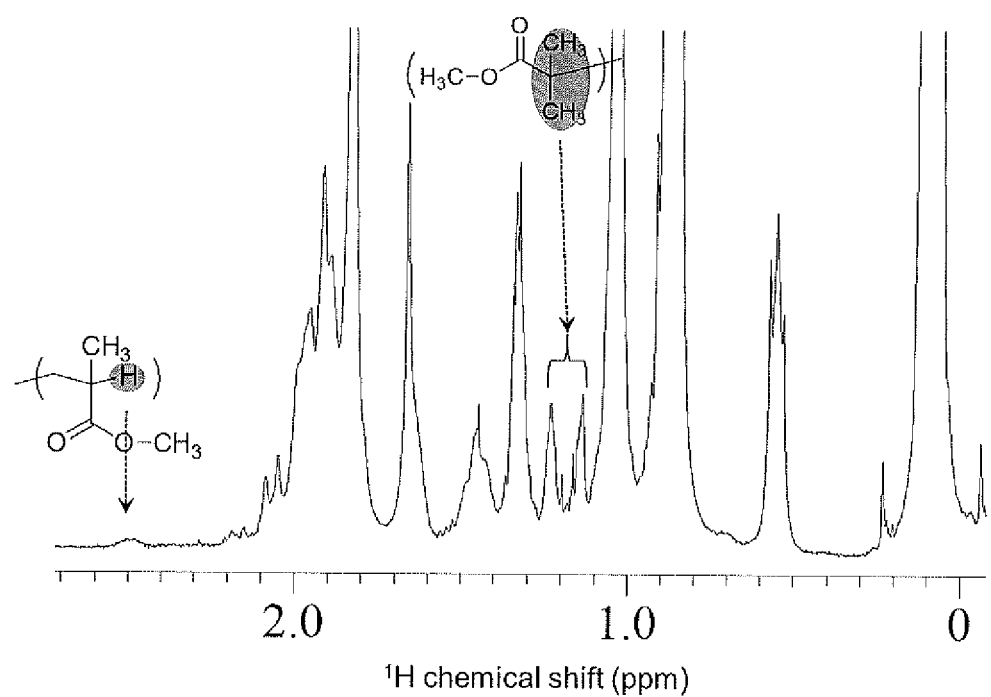
FIG. 2 is an enlarged partial view of the $^1$H-NMR spectra of the copolymer prepared in Example 1.

In a three-necked flask, 19.9 mg of tetrabutylammonium m-chlorobenzoate dried under reduced pressure was placed and dissolved by adding 25 mL of THF. In a nitrogen atmosphere, 436 mg of dimethylketene methyltrimethylsilyl acetal was added, and a monomer mixture of 10 g of methyl methacrylate (MMA) and 10 g of a monomer (a) represented by the following formula was added dropwise over 30 minutes. After stirring at room temperature for an additional 30 minutes, the reaction was stopped by adding 4 mL of methanol. The reaction mixture was subjected to distillation at 150 degrees C. and reduced pressure for 1 hour to obtain a copolymer. The obtained copolymer was dissolved in deuterochloroform and subjected to $^1$H-NMR spectrometry. The $^1$H-NMR spectra showed that it is a copolymer represented by the following formula (7). $^1$H-NMR chart is as shown in FIG. 1 and FIG. 2. FIG. 1 is an overall view of the $^1$H-NMR chart, and FIG. 2 is an enlarged partial view of the $^1$H-NMR chart, showing a terminal structure.

In addition, a number average molecular weight and polydispersity (Mw/Mn), reduced to polystyrene, were determined by GPC. The residual monomer(s) were quantified by GC-MS. The results were as follows.
Number average molecular weight (Mn)=11,700,
Polydispersity (Mw/Mn)=1.24
Residual monomer amount (MMA) was less than 1 ppm.

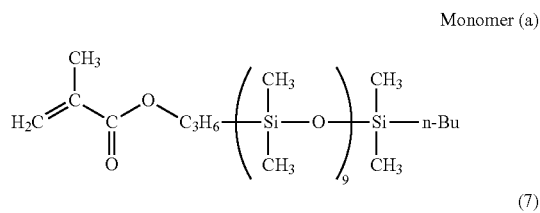

Monomer (a)

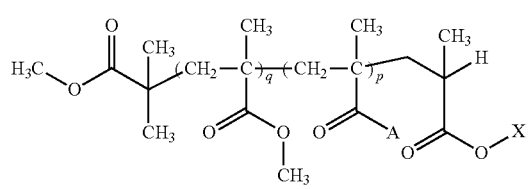

(7)

In the formula (7), A is a residue of the monomer (a), X is a methyl group or a residue of the monomer (a), p and q are the numbers such that the copolymer had the aforesaid number average molecular weight, and each unit shown in parentheses is randomly bonded.

Example 2

In a three-necked flask, 19.9 mg of tetrabutylammonium m-chlorobenzoate dried under reduced pressure was placed and dissolved by adding 25 mL of THF. In a nitrogen atmosphere, 436 mg of dimethylketene methyltrimethylsilyl acetal was added and a monomer mixture of 15 g of methyl methacrylate and 15 g of the aforesaid monomer (a) was added dropwise over 30 minutes. After stirring at room temperature for an additional 30 minutes, the reaction was stopped by adding 4 mL of methanol. The reaction mixture was subjested to distillation at 150 degrees C. and reduced pressure for 1 hour to obtain a copolymer. The obtained copolymer was dissolved in deuterochloroform and subjected to $^1$H-NMR spectrometry. The $^1$H-NMR spectra showed that it is a copolymer represented by the aforesaid formula (7). In addition, a number average molecular weight and polydispersity (Mw/Mn), reduced to polystyrene, were determined by GPC. Further, residual monomer(s) were quantified by GC-MS. The results are as follows.
Number average molecular weight (Mn)=15,100,
Polydispersity (Mw/Mn)=1.28
Residual monomer amount (MMA) was less than 1 ppm.

Example 3

In a three-necked flask, 19.9 mg of tetrabutylammonium m-chlorobenzoate dried under reduced pressure was placed and dissolved by adding 25 mL of THE. In a nitrogen atmosphere, 436 mg of dimethylketene methyltrimethylsilyl acetal e was added and a monomer mixture of 20 g of methyl methacrylate and 20 g of the aforesaid monomer (a) was added dropwise over 30 minutes. After stirring at room temperature for an additional 30 minutes, the reaction was stopped by adding 4 mL of methanol. The reaction mixture was subjected to distillation at 150 degrees C. and reduced pressure for 1 hour to obtain a copolymer. The obtained copolymer was dissolved in deuterochloroform and subjected to $^1$H-NMR spectrometry. The $^1$H-NMR spectra showed that it is a copolymer represented by the aforesaid formula (7). In addition, a number average molecular weight and polydispersity (Mw/Mn), reduced to polystyrene, were determined by GPC. Further, residual monomers were quantified by GC-MS. The results are as follows.
Number average molecular weight (Mn)=20,400
Polydispersity (Mw/Mn)=1.34
Residual monomer amount (MMA) was less than 1 ppm.

Example 4

In a three-necked flask, 19.9 mg of tetrabutylammonium m-chlorobenzoate dried under reduced pressure was placed and dissolved by adding 25 mL of THF. In a nitrogen atmosphere, 436 mg of dimethylketene methyltrimethylsilyl acetal was added and a monomer mixture of 7.1 g of methyl methacrylate, 1.6 g of n-butyl methacrylate (B MA), 1.8 g of 2-ethylhexyl methacrylate (2 EHMA) and 10.0 g of the monomer (b) was added dropwise over 30 minutes. After stirring at room temperature for an additional 30 minutes, the reaction was stopped by adding 4 mL of methanol. Thereafter, the reaction mixture was subjected to distillation at 150 degrees C. and reduced pressure for 1 hour. when residual monomers were determined by GC-MS, the monomer remained. Therefore, strip was again carried out at 150 degrees C. for 1 hour to obtain a copolymer. The obtained copolymer was dissolved in deuterochloroform and subjected to $^1$H-NMR spectrometry. The $^1$H-NMR spectra showed that it is a copolymer represented by the following formula (8). In addition, a number average molecular weight and polydispersity (Mw/Mn), reduced to polystyrene, were determined by GPC. Further, residual monomer(s) were quantified by GC-MS. The results are as follows.
Number average molecular weight (Mn)=10,700
Polydispersity (Mw/Mn)=1.27
The Residual Monomer Amount
    [After Vacuum Distillation]
    The amount of MMA was less than 1 ppm, the amount of BMA was 20 ppm (BMA), and the amount of 2 EHMA was 23 ppm.
    [After Second Vacuum Distillation]
    The amount of MMA was less than 1 ppm, the amount of BMA was less than 1 ppm, and the amount of 2 EHMA was less than 1 ppm.

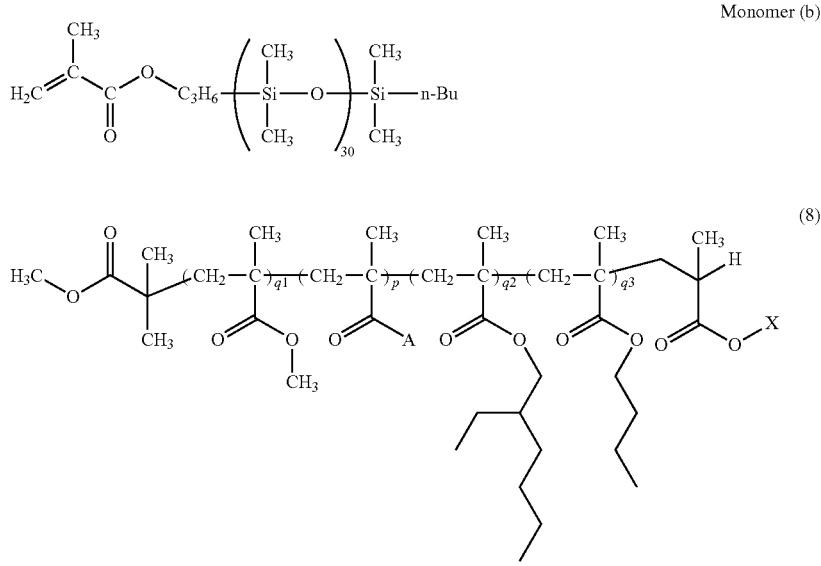

In the formula (8), A is a residue of the monomer (b), X is a methyl group, an n-butyl group, a 2-ethylhexyl group or a residue of the monomer (b), p, $q^1$, $q^2$ and $q^3$ are numbers such that the copolymer has the aforesaid number average molecular weight, and each unit shown in parentheses is randomly bonded.

Example 5

In a three-necked flask, 19.9 mg of tetrabutylammonium m-chlorobenzoate dried under reduced pressure was placed and dissolved by adding 25 mL of THF. In a nitrogen atmosphere, 436 mg of dimethyl ketene methyl trimethylsilyl acetal was added and a monomer mixture of 10.5 g of methyl methacrylate, 2.3 g of n-butyl methacrylate, 2.5 g of 2-ethylhexyl methacrylate and 15 g of the monomer (b) was added dropwise over 30 minutes. After stirring at room temperature for an additional 30 minutes, the reaction was stopped by adding 4 mL of methanol. Thereafter, the reaction mixture was distilled off under reduced pressure at 150 degrees C. for 1 hour. When residual monomer was determined by GC-MS, the monomer remained. Therefore, strip was again carried out at 150 degrees C. for 1 hour to obtain a copolymer. The obtained copolymer was dissolved in deuterochloroform and subjected to $^1$H-NMR spectrometry. The $^1$H-NMR spectra showed that it is a copolymer represented by the aforesaid formula (8). In addition, a number average molecular weight and polydispersity (Mw/Mn), reduced to polystyrene, were determined by GPC. Further, residual monomers were quantified by GC-MS. The results are as follows.
Number average molecular weight (Mn)=17,800
Polydispersity (Mw/Mn)=1.38
The Residual Monomer Amount:
[After Vacuum Distillation]
The amount of MMA was less than 1 ppm, the amount of BMA was 34 ppm (BMA), and the amount of 2 EHMA was 50 ppm.
[After Second Vacuum Distillation]
The amount of MMA was less than 1 ppm, the amount of BMA was less than 1 ppm, and the amount of 2 EHMA was less than 1 ppm.

Example 6

In a three-necked flask, 19.9 mg of tetrabutylammonium m-chlorobenzoate dried under reduced pressure was placed and dissolved by adding 25 mL of THE. In a nitrogen atmosphere, 936 mg of dimethyl ketene methyl trimethylsilyl acetal was added and a monomer mixture of 14.0 g of methyl methacrylate, 3.0 g of n-butyl methacrylate, 3.2 g of 2-ethylhexyl methacrylate and 20 g of the monomer (b) was added dropwise over 30 minutes. After stirring at room temperature for an additional 30 minutes, the reaction was stopped by adding 4 mL of methanol. Thereafter, the reaction mixture was subjected to distillation at 150 degree C. and reduced pressure for 1 hour. When residual monomer was determined by GC-MS, the monomer remained. Therefore, strip was again carried out at 150 degrees C. for 1 hour to obtain a copolymer. The obtained copolymer was dissolved in deuterochloroform and subjected to $^1$H-NMR spectrometry. The $^1$H-NMR spectra showed that it is a copolymer represented by the aforesaid formula (8). In addition, a number average molecular weight and polydispersity (Mw/Mn), reduced to polystyrene, were determined by GPC. Further, residual monomer(s) were quantified by GC-MS. The results are as follows.
Number average molecular weight (Mn)=21,500
Polydispersity (Mw/Mn)=1.42
The Residual Monomer Amount:
[After Vacuum Distillation]
The amount of MMA was less than 1 ppm, the amount of BMA was 44 ppm (BMA), and the amount of 2 EHMA was 60 ppm.
[After Second Vacuum Distillation]
The amount of MMA was less than 1 ppm, the amount of BMA was less than 1 ppm, and the amount of 2 EHMA was less than 1 ppm.

Example 7

In a three-necked flask 19.9 mg of tetrabutylammonium m-chlorobenzoate dried under reduced pressure was placed and dissolved by adding 25 mL of THF. In a nitrogen atmosphere, 436 mg of dimethylketene methyl trimethylsilyl acetal was added and a monomer mixture of 10 g of methyl methacrylate and 10 g of the following monomer (c) was added dropwise over 30 minutes. After stirring at room temperature for an additional 30 minutes, the reaction was stopped by adding 4 mL of methanol. Thereafter, the reaction mixture was subjected to distillation at 150 degrees and reduced pressure for 1 hour to obtain a copolymer. The obtained copolymer was dissolved in deuterochloroform and subjected to $^1$H-NMR spectrometry. The $^1$H-NMR spectra showed that it is a copolymer represented by the following formula (9). In addition, a number average molecular weight and polydispersity (Mw/Mn), reduced to polystyrene, were determined by GPC. Further, residual monomer(s) were quantified by GC-MS. The results are as follows.
Number average molecular weight (Mn)=11,340
Polydispersity (Mw/Mn)=1.32
The amount of the residual monomer (MMA) was less than 1 ppm.

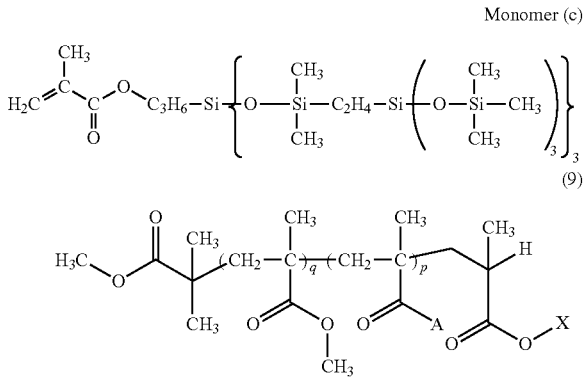

In the formula (9), A is a residue of the monomer (c), X is a methyl group or a residue of the monomer (c), p and q are the numbers such that the copolymer had the aforesaid number average molecular weight, and each unit shown in parentheses is randomly bonded.

Example 8

In a three-necked flask, 19.9 mg of tetrabutylammonium m-chlorobenzoate dried under reduced pressure was placed and dissolved by adding 25 mL of THF. In a nitrogen atmosphere, 436 mg of dimethyl ketene methyl trimethylsilyl acetal was added and a monomer mixture of 7.1 g of methyl methacrylate, 1.6 g of n-butyl methacrylate, 1.8 g of 2-ethylhexyl methacrylate and 10 g of the above monomer (c) was added dropwise over 30 minutes. After stirring at room temperature for an additional 30 minutes, the reaction was stopped by adding 4 mL of methanol. Thereafter, the reaction mixture was subjected to distillation at 150 degrees C. and reduced pressure for 1 hour. When residual monomer was determined by GC-MS, the monomer remained. Therefore, strip was again carried out at 150 degrees C. for 1 hour to obtain a copolymer. The obtained copolymer was dissolved in deuterochloroform and subjected to $^1$H-NMR spectrometry. The $^1$H-NMR spectra showed that it is a copolymer represented by the following formula (10). In addition, a number average molecular weight and polydispersity (Mw/Mn), reduced to polystyrene, were determined by GPC. Further, residual monomers were quantified by GC-MS. The results are as follows.

Number average molecular weight (Mn)=10,800,
Polydispersity (Mw/Mn)=1.33
The Residual Monomer Amount:
 [After Vacuum Distillation]
 The amount of MMA was less than 1 ppm, the amount of BMA was 25 ppm (BMA), and the amount of 2 EHMA was 51 ppm.
 [After Second Vacuum Distillation]
 The amount of MMA was less than 1 ppm, the amount of BMA was less than 1 ppm, and the amount of 2 EHMA was less than 1 ppm.

C. and reduced pressure for 1 hour to obtain a copolymer. The obtained copolymer was dissolved in deuterochloroform and subjected to $^1$H-NMR spectrometry. The $^1$H-NMR spectra showed that it is a copolymer represented by the following formula (11). In addition, a number average molecular weight and polydispersity (Mw/Mn), reduced to polystyrene, were determined by GPC. Further, residual monomers were quantified by GC-MS. The results are as follows.

Number average molecular weight (Mn)=12,340

Polydispersity (Mw/Mn)=1.18

The amount of the residual monomer (2 EHA) was 42 ppm.

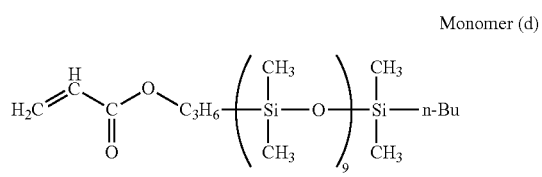

Monomer (d)

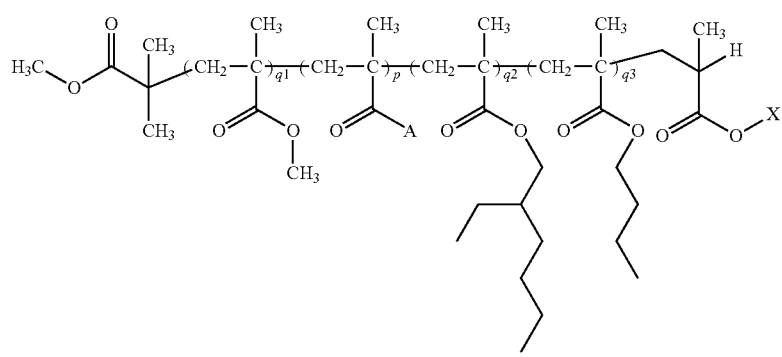

(10)

In the formula (10), A is a residue of the monomer (c), X is a methyl group, an n-butyl group, a 2-ethylhexyl group or a residue of the monomer (c) p, $q^1$, $q^2$ and $q^3$ are numbers such that the copolymer had the aforesaid number average molecular weight, and each unit shown in parentheses is randomly bonded.

Example 9

In a three-necked flask, 25 mL of toluene, 436 mg of dimethylketene methyltrimethylsilyl acetal, 10.0 g of 2-ethylhexyl acrylate (2 EHA) and 10.0 g of the following monomer (d) were added and stirred. 400 μL of toluene solution containing 50 mM of 1-[bis(trifluoromethanesulfonyl)methyl]-2,3,4,5,6-pentafluoro benzene was further added thereto and stirred. After stirring for 1 hour, the reaction was stopped by adding 4 mL of methanol. Thereafter, the mixture was subjected to distillation at 150 degrees -continued

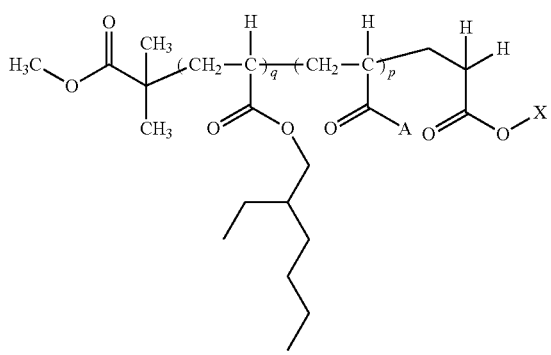

(11)

In the formula (11), A is a residue of the monomer (d), X is a 2-ethylhexyl group or a residue of the monomer (d), p and q are numbers such that the copolymer had the aforesaid number average molecular weight, and each unit shown in parentheses is randomly bonded.

Example 10

In a three-necked flask, 25 mL of toluene, 436 mg of dimethylketene methyltrimethylsilyl acetal, 10.0 g of dimethylacrylamide (DMAA) and 10.0 g of the aforesaid monomer (d) were placed and stirred. 400 µL of toluene solution containing 50 mM of 1-[bis(trifluoromethanesulfonyl)methyl]-2,3,4,5,6-pentafluoro benzene was further added thereto and stirred. After stirring for 1 hour, the reaction was stopped by adding 4 mL of methanol. Thereafter, the mixture was subjected to distillation at 150 degrees C. and reduced pressure for 1 hour to obtain a copolymer. The obtained copolymer was dissolved in deuterochloroform and subjected to $^1$H-NMR spectrometry. The $^1$H-NMR spectra showed that it is a copolymer represented by the following formula (12). In addition, a number average molecular weight and polydispersity (Mw/Mn), reduced to polystyrene, were determined by GPC. Further, residual monomers were quantified by GC-MS. The results are as follows.

Number average molecular weight (Mn)=11,920

Polydispersity (Mw/Mn)=1.24

The amount of the residual monomer (DMAA) was 32 ppm.

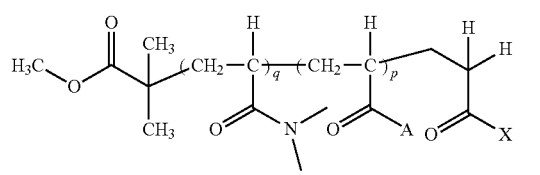

(12)

In the formula (12), A is the residue of the monomer (d), X is the residue of dimethylacrylamide or the residue of the monomer (d) p and q are numbers such that the copolymer had the aforesaid number average molecular weight, and each unit shown in parentheses is randomly bonded.

Example 11

In a three-necked flask, 25 mL of toluene, 436 mg of dimethylketene methyltrimethylsilyl acetal, 9.0 g of 2-ethylhexyl acrylate, 1.0 g of dimethylacrylamide and 10.0 g of the aforesaid monomer (d) were added and stirred. 400 µL of toluene solution containing 50 mM of 1-[bis(trifluoromethanesulfonyl)methyl]-2,3,4,5,6-pentafluoro benzene was further added thereto and stirred. After stirring for 1 hour, the reaction was stopped by adding 4 mL of methanol. Thereafter, the mixture was subjected to distillation at 150 degrees C. and reduced pressure for 1 hour to obtain a copolymer. The obtained copolymer was dissolved in deuterochloroform and subjected to $^1$H-NMR spectrometry. The $^1$H-NMR spectra showed that it is a copolymer represented by the following formula (13). In addition, a number average molecular weight and polydispersity (Mw/Mn), reduced to polystyrene, were determined by GPC. Further, residual monomers were quantified by GC-MS. The results are as follows.

Number average molecular weight (Mn)=12,030

Polydispersity (Mw/Mn)=1.19

Residual Monomer Amounts:

The amount of 2 FHA was 33 ppm and the amount of DMAA was 29 ppm.

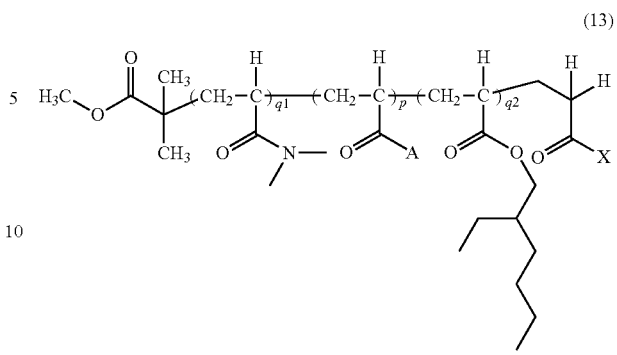

(13)

In the formula (13), A is the residue of the monomer (d), X is the residue of 2-ethylhexyl acrylate, a residue of dimethylacrylamide or a residue of the monomer (d), p, $q^1$ and $q^2$ are numbers such that the copolymer had the aforesaid number average molecular weight, and each unit shown in parentheses is randomly bonded.

Example 12

In a three-necked flask, 19.9 mg of tetrabutylammonium m-chlorobenzoate dried under reduced pressure was placed and dissolved by adding 25 mL of THF. Under a nitrogen atmosphere, 436 mg of dimethylketene methyltrimethylsilyl acetal was added, 10.0 g of methyl methacrylate was added dropwise over 15 minutes, and further stirred for 15 minutes. Next, 10.0 g of the aforesaid monomer (a) was added dropwise over 15 minutes. After further stirring at room temperature for 15 minutes, the reaction was stopped by adding 4 mL of methanol. Thereafter, the mixture was subjected to distillation at 150 degrees C. and reduced pressure for 1 hour to obtain a copolymer. The $^1$H-NMR spectra showed that it is a copolymer, i.e. AB block copolymer, represented by the following formula (14). In addition, a number average molecular weight and polydispersity (Mw/Mn), reduced to polystyrene, were determined by GPC. Further, residual monomers were quantified by GC-MS. The results are as follows.

Number average molecular weight (Mn)=10,800

Polydispersity (Mw/Mn)=1.08

The amount of residual monomer (MMA) was less than 1 ppm.

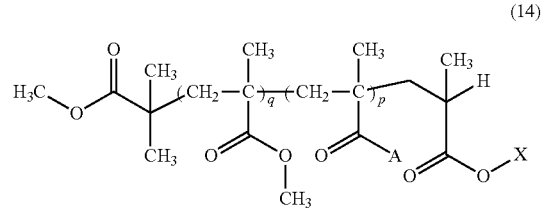

(14)

In the formula (14), A is a residue of the monomer (a), X is a methyl group or a residue of the monomer (a), p and q are numbers such that the copolymer had the aforesaid number average molecular weight, and each unit shown in parentheses forms an AB block structure.

Example 13

In a three-necked flask, 19.9 mg of tetrabutylammonium m-chlorobenzoate dried under reduced pressure was placed and dissolved by adding 25 mL of THF. In a nitrogen atmosphere, 436 mg of dimethylketene methyltrimethylsilyl acetal was added, 5.0 g of methyl methacrylate was added dropwise over 10 minutes, and further stirred for 10 minutes.

Next, 5.0 g of the aforesaid monomer (a) was added dropwise over 10 minutes, and the mixture was stirred for 10 minutes. In the same manner, 5.0 g of methyl methacrylate and 5.0 g of the monomer (a) were further added dropwise and stirred. The reaction was stopped by adding 4 mL of methanol. Thereafter, the mixture was subjected to distillation at 150 degrees C. and reduced pressure for 1 hour to obtain a copolymer. The $^1$H-NMR spectra showed that it is a copolymer, i.e. ABAB block copolymer, represented by the following formula (15). In addition, a number average molecular weight and polydispersity (Mw/Mn), reduced to polystyrene, were determined by GPC. Further, residual monomers were quantified by GC-MS. The results are as follows.
Number average molecular weight (Mn)=11,100
Polydispersity (Mw/Mn)=1.10
Residual monomer amount (MMA) was less than 1 ppm.

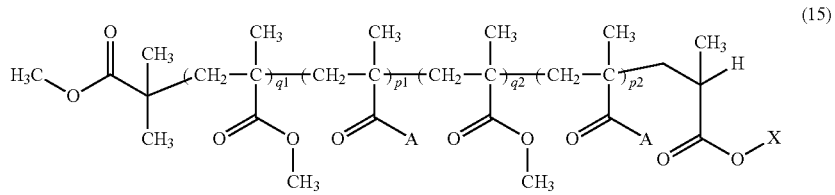

(15)

In the formula (15), A is a residue of the monomer (a), X is a methyl group or a residue of the monomer (a), p and q are numbers such that the copolymer had the aforesaid number average molecular weight, and each unit shown in parentheses forms an ABAB block structure.

Example 14

In a three-necked flask, 19.9 mg of tetrabutylammonium m-chlorobenzoate dried under reduced pressure was placed and dissolved by adding 25 mL of THF. In a nitrogen atmosphere, 436 mg of dimethylketene methyl trimethylsilyl acetal was added and a monomer mixture of 15 g of lauryl methacrylate (LMA) and 15 g of the aforesaid monomer (a) was added dropwise over 30 minutes. After further stirring at room temperature for 30 minutes, the reaction was stopped by adding 4 mL of methanol. Thereafter, the mixture was subjected to distillation at 180 degrees C. and reduced pressure for 1 hour to obtain a copolymer. The $^1$H-NMR spectra showed that it is a copolymer represented by the following formula (16). In addition, a number average molecular weight and polydispersity (Mw/Mn), reduced to polystyrene, were determined by GPC. Further, residual monomers were quantified by GC-MS. The results are as follows.
Number average molecular weight (Mn)=16,400
Polydispersity (Mw/Mn)=1.22
Residual monomer amount (LMA) was 28 ppm.

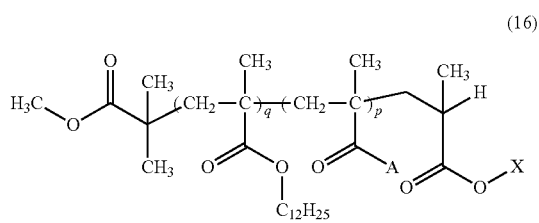

(16)

In the formula (16), A is a residue of the monomer (a), X is a residue of lauryl methacrylate or a residue of the monomer (a), p and q are the numbers such that the copolymer had the aforesaid number average molecular weight, and each unit shown in parentheses is randomly bonded.

Example 15

In a three-necked flask, 19.9 mg of tetrabutylammonium m-chlorobenzoate dried under reduced pressure was placed and dissolved by adding 25 mL of THF. In a nitrogen atmosphere, 436 mg of dimethylketene methyltrimethylsilyl acetal was added and a monomer mixture of 15 g of stearyl methacrylate (SMA) and 15 g of the aforesaid monomer (a) was added dropwise over 30 minutes. The mixture was further stirred for 30 minutes and the reaction was stopped by adding 4 mL of methanol. Thereafter, the mixture was subjected to distillation at 180 degrees C. and reduced pressure for 1 hour to obtain a copolymer. The $^1$H-NMR spectra showed that it is a copolymer represented by the following formula (17). In addition, a number average molecular weight and polydispersity (Mw/Mn), reduced to polystyrene, were determined by GPC. Further, residual monomers were quantified by GC-MS. The results are as follows.
Number average molecular weight (Mn)=15,530
Polydispersity (Mw/Mn)=1.30
Residual monomer amount (SMA) was 42 ppm.

(17)

In the formula (17), A is the residue of the monomer (a), X is the residue of stearyl methacrylate or the residue of the monomer (a), p and q are the numbers such that the copolymer has the aforesaid number average molecular weight, and each unit shown in parentheses is randomly bonded.

Example 16

In a three-necked flask, 19.9 mg of tetrabutylammonium m-chlorobenzoate dried under reduced pressure was placed and dissolved by adding 25 mL of THF. In a nitrogen atmosphere, 436 mg of dimethylketene methyltrimethylsilyl acetal was added and a monomer mixture of 10 g of 2-ethoxyethyl methacrylate (EEMA) and 10 g of the aforesaid monomer (a) was added dropwise over 30 minutes. The mixture was further stirred for 30 minutes and the reaction was stopped by adding 4 mL of methanol. Thereafter, the mixture was subjected to distillation at 150 degrees C. and reduced pressure for 1 hour to obtain a copolymer. It was confirmed from the $^1$H-NMR spectrum that it is a copolymer represented by the following formula (18). In addition, number average molecular weight and polydispersity (Mw/Mn), reduced to polystyrene, were determined by GPC. Further, residual monomers were quantified by GC-MS. The results are as follows.

Number average molecular weight (Mn)=11,030

Polydispersity (Mw/Mn)=1.12

Residual monomer amount (NEMA) was 38 ppm.

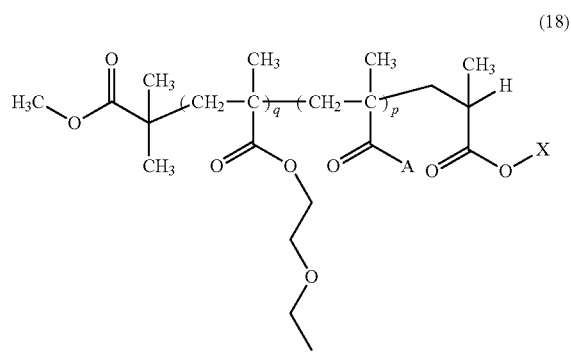

(18)

In the formula (18), A is a residue of the monomer (a), X is a residue of 2-ethoxyethyl methacrylate or a residue of the monomer (a), p and q are the numbers such that the copolymer has the aforesaid number average molecular weight, and each unit shown in parentheses is randomly bonded.

Example 17

In a three-necked flask, 19.9 mg of tetrabutylammonium m-chlorobenzoate dried under reduced pressure was placed and dissolved by adding 25 mL of THF. In nitrogen atmosphere, 541 mg of dimethylketene methyltriethylsilyl acetal was added and the monomer mixture of 10 g of methyl methacrylate (MMA) and 10 g of the aforesaid monomer (a) was added dropwise over 30 minutes. The mixture was further stirred for 30 minutes and the reaction was stopped by adding 4 mL of methanol. Thereafter, the mixture was subjected to distillation at 150 degrees C. and reduced pressure for 1 hour to obtain a copolymer. The $^1$H-NMR spectra showed that it is a copolymer represented by the following formula (19). In addition, number average molecular weight and polydispersity (Mw/Mn), reduced to polystyrene, were determined by GPC. Further, residual monomers were quantified by GC-MS. The results are as follows.

Number average molecular weight (Mn)=11,230

Polydispersity (Mw/Mn)=1.29

Residual monomer amount (MMA) was less than 1 ppm.

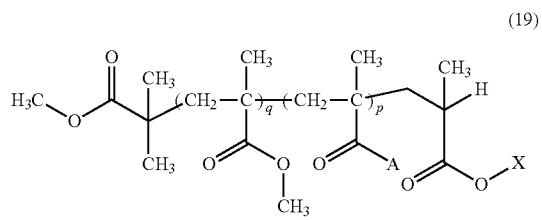

(19)

In the formula (19), A is a residue of the monomer (a), X is a methyl group or a residue of the monomer (a), p and q are the numbers such that the copolymer had the aforesaid number average molecular weight, and each unit shown in parentheses is randomly bonded.

Comparative Example 1

16 Grams of toluene were placed in a separable flask and heated to 100 degrees C. in an oil bath. A mixture of a monomer and a radical initiator (20 g of methyl methacrylate, 20 g of the aforesaid monomer (a), and 4.39 g of t-butylperoxy-2-ethylhexanoate (PERBUTYL O, trade mark)) was added dropwise thereto over 3 hours. The mixture was stirred at 100 degrees C. for 2 hours, and further 0.46 g of PERBUTYL O was added. Thereafter, the mixture was stirred at 100 degrees C. for 3 hours and returned to room temperature. The mixture was subjected to distillation at 150 degrees C. and reduced pressure for 1 hour to obtain a methacrylic silicone graft copolymer represented by the following formula (20). Number average molecular weight and polydispersity (Mw/Mn), reduced to polystyrene, were determined by GPC. Further, residual monomers were quantified by GC-MS. The results are as follows.

Number average molecular weight (Mn)=10,200

Polydispersity (Mw/Mn)=1.80

Residual monomer amount (MMA) was 930 ppm.

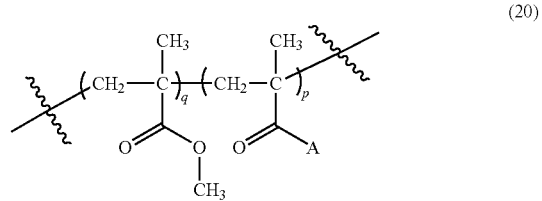

(20)

In the formula (20), A is a residue of the monomer (a), p and q are the numbers such that the copolymer had the aforesaid number average molecular weight, and each unit shown in parentheses is randomly bonded.

Comparative Example 2

16 Grams of toluene were placed in a separable flask and heated to 100 degrees C. in an oil bath. A mixture of a monomer and a radical initiator (20 g of methyl methacrylate, 20 g of the aforesaid monomer (a) and 2.63 g of PERBUTYL O, trade mark) was added dropwise thereto over 3 hours. The mixture was stirred at 100 degrees C. for 2 hours, and then 0.58 g of PERBUTYL O was added. Thereafter, the mixture was stirred at 100 degrees C. for 3 hours and returned to room temperature. The mixture was subjected to distillation at 150 degrees C. and reduced pressure for 1 hour to obtain the aforesaid methacrylic silicone graft copolymer represented by the formula (20). Number average molecular weight and polydispersity (Mw/Mn), reduced to polystyrene, were determined by GPC. Further, residual monomers were quantified by GC-MS. The results are as follows.

Number average molecular weight (Mn)=18,000

Polydispersity (Mw/Mn)=2.23

Residual monomer amount (MMA) was 1120 ppm.

Comparative Example 3

16 Grams of toluene were placed in a separable flask and heated to 100 degrees C. in an oil bath. A mixture of a monomer and a radical initiator (20 g of methyl methacrylate, 20 g of the aforesaid monomer (a) and 1.48 g of PERBUTYL O, trade mark) was added dropwise thereto over 3 hours. The mixture was stirred at 100 degrees C. for 2 hours, and further 0.29 g of PERBUTYL O was added. Thereafter, the mixture was stirred at 100 degrees C. for 3 hours and returned to room temperature. The mixture was subjected to distillation at 150 degrees C. and reduced pressure for 1 hour to obtain a methacrylic silicone graft copolymer represented by the aforesaid formula (20). Number average molecular weight and polydispersity (Mw/Mn), reduced to polystyrene, were determined by GPC. Further, residual monomers were quantified by GC-MS. The results are as follows.

Number average molecular weight (Mn)=22,300

Polydispersity (Mw/Mn)=2.00

Residual monomer amount (MMA) was 994 ppm.

In the preparation methods of Comparative Examples 1 to 3, plural terminal stopping reactions occurred and, therefore, it was difficult to determine the terminal structure of the methacrylic silicone graft copolymer represented by the aforesaid formula (20).

Comparative Example 4

48 Grams of toluene were placed in a separable flask and heated to 100 degrees C. in an oil bath. A mixture of monomer and radical initiator (31.5 g of methyl methacrylate, 6.8 g of n-butyl methacrylate, 7.3 g of 2-ethylhexyl methacrylate, 45.0 g of monomer (b) and 2.7 g of PERBUTYL 0, trade mark) was added dropwise thereto over 3 hours. The mixture was stirred at 100 degrees C. for 2 hours, and further 0.42 g of PERBUTYL O was added. Thereafter, the mixture was stirred at 100 degrees C. for 3 hours and returned to room temperature. The mixture was subjected to distillation at 150 degrees C. and reduced pressure for 1 hour to obtain a methacrylic silicone graft copolymer represented by the following formula (21). Number average molecular weight and polydispersity (Mw/Mn), reduced to polystyrene, were determined by GPC. Further, residual monomers were quantified by GC-MS. The results are as follows.

Number average molecular weight (Mn)=12,500

Polydispersity (Mw/Mn)=1.88

Residual Monomer Amounts:

The amount of MMA was 1150 ppm, the amount of BMA was 773 ppm, and the amount of 2 EHMA was 750 ppm.

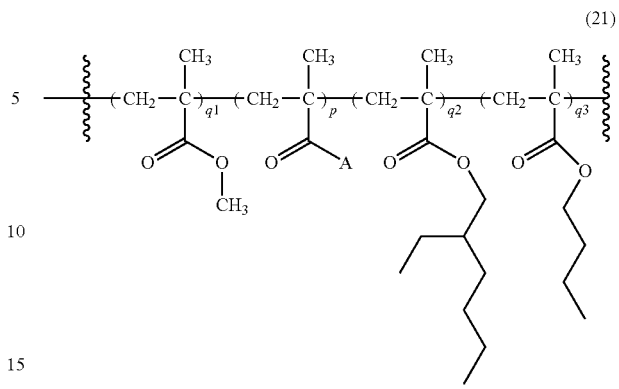

(21)

In the formula (21), A is a residue of the monomer (b) p, $q^1$, $q^2$ and $q^3$ are the numbers such that the copolymer had the aforesaid number average molecular weight, and each unit shown in parentheses is randomly bonded.

Comparative Example 5

24 Grams of toluene was placed in a separable flask and heated to 100 degrees C. in an oil bath. A mixture of a monomer and a radical initiator (15.7 g of methyl methacrylate, 3.37 g of n-butyl methacrylate, 3.64 g of 2-ethylhexyl methacrylate, 22.5 g of the aforesaid monomer (b) and 1.07 g of PERBUTYL O, trade mark) was added dropwise thereto over 3 hours. The mixture was stirred at 100 degrees C. for 2 hours, and further 0.44 g of PERBUTYL O was added. Thereafter, the mixture was stirred at 100 degrees C. for 3 hours and returned to room temperature. The mixture was subjected to distillation at 150 degrees C. and reduced pressure for 1 hour to obtain a methacrylic silicone graft copolymer represented by the aforesaid formula (21). Number average molecular weight and polydispersity (Mw/Mn), reduced to polystyrene, were determined by GPC. Further, residual monomers were quantified by GC-MS. The results are as follows.

Number average molecular weight (Mn)=20,800

Polydispersity (Mw/Mn)=1.54

Residual Monomer Amounts:

The amount of MMA was 1125 ppm, the amount of BMA was 762 ppm, and the amount of 2 EHMA was 789 ppm.

Comparative Example 6

24 Grams of toluene was placed in a separable flask and heated to 100 degrees C. is an oil bath. A mixture of a monomer and a radical initiator (15.7 g of methyl methacrylate, 3.37 g of n-butyl methacrylate, 3.64 g of 2-ethylhexyl methacrylate, 22.5 g of the above monomer (b) and 0.72 g of PERBUTYL O, trade mark) was added dropwise thereto over 3 hours. The mixture was stirred at 100 degrees C. for 2 hours, and further 0.31 g of PERBUTYL O was added. Thereafter, the mixture was stirred at 100 degrees C. for 3 hours and returned to room temperature. The mixture was distilled off under reduced pressure at 150 degrees C. for 1 hour to obtain a methacrylic silicone graft copolymer represented by the aforesaid formula (21). Number average molecular weight and polydispersity (Mw/Mn), reduced to polystyrene, were determined by GPC. Further, residual monomers were quantified by GC-MS. The results are as follows.

Number average molecular weight (Mn)=24,600,
Polydispersity (Mw/Mn)=2.30
Residual Monomer Amounts:

The amount of MMA was 1015 ppm, the amount of BMA was 820 ppm, and the amount of 2 EHMA was 791 ppm.

In the preparation methods of Comparative Examples 4 to 6, plural terminal stopping reactions occurred and, therefore, it was difficult to determine the terminal structure of the methacrylic silicone graft copolymer represented by the aforesaid formula (21).

[Thermogravimetric Analysis]

The thermogravimetric analysis of the copolymers obtained in Examples 1 to 6 and Comparative Examples 1 to 6 was carried out and the 50% weight loss temperature was determined. The measuring method will be described below in detail.

Each of the copolymer was subjected to stripping at 150 degrees C. for 1 hour and about 10 mg of the copolymer was taken up to prepare a sample cell. The sample cell was set in a thermogravimetric analyzer (TGA Q 500, ex TA Instruments), the temperature was raised from 0 degrees C. to 600 degrees C. (heating rate: 10 degrees C./min) in a nitrogen atmosphere. The change in weight was determined. The temperature at which loss of the weight of the sample reached a half of the initial weight was taken as the "50% weight loss temperature".

The results are as shown in Table 1. In Examples 1 to 6, the 50% weight loss temperature was higher than 360 degrees C., so that the heat resistance was higher, compared to those in the Comparative Examples.

TABLE 1

|  | Ex. 1 | Ex. 2 | Ex. 3 | Ex. 4 | Ex. 5 | Ex. 6 |
|---|---|---|---|---|---|---|
| 50% weight loss temperature (degrees C.) | 373 | 368 | 363 | 377 | 374 | 373 |

TABLE 1-continued

|  | Com. Ex. 1 | Com. Ex. 2 | Com. Ex. 3 | Com. Ex. 4 | Com. Ex. 5 | Com. Ex. 6 |
|---|---|---|---|---|---|---|
| 50% weight loss temperature (degrees C.) | 326 | 326 | 322 | 336 | 356 | 353 |

Examples 18 to 20 and Comparative Examples 7 to 11

Evaluation of Oily Foundation

Using the (meth) acrylic silicone graft copolymer (A) obtained in Examples 1, 3 and 6, an oily foundations were prepared according to the following method. The compositions are as shown in the following Table 2.

(Preparation Method)

Step A: Components 1 to 12 were heated to dissolve.
Step B: Components 13 to 16 were mixed with the mixture obtained in step A.
Step C: The mixture obtained in step B was homogeneously mixed with a three-roll kneader.
Step D: The mixture obtained in step C was heated to dissolve, then degassed, filled in a metal dish and cooled to obtain an oily foundation.

The properties in use of the obtained oily foundations was evaluated, based on the following criteria.

The tests for properties in use were conducted by 50 females panelists. The oily foundations were evaluated on the gloss, the extension on the skin, the feeling of close contact and the goodness of fit at the time of application, the non-stickiness, the moist feeling, the beauty of the finish and make-up retention, according to the criteria as shown in Table 3. The score were averaged for each item and given a grade shown in Table 4. The results are as shown in Table 5.

As seen from Table 5, the oily foundations obtained in Examples 18 to 20 shows excellent gloss and extension on the skin, has excellent feeling of close contact, goodness of fit, less stickiness and moist finish, and makeup retention was also very good, compared to the oily foundations obtained in Comparative Examples 7 to 11.

TABLE 2

| Component | Example(%) | | | Comparative Example (%) | | | | |
|---|---|---|---|---|---|---|---|---|
|  | 18 | 19 | 20 | 7 | 8 | 9 | 10 | 11 |
| 1. Starch fatty acid ester | 6.0 | 6.0 | 6.0 | 6.0 | 6.0 | 6.0 | 6.0 | 6.0 |
| 2. Ceresin | 7.0 | 7.0 | 7.0 | 7.0 | 7.0 | 7.0 | 7.0 | 7.0 |
| 3. Polybutene | 4.0 | 4.0 | 4.0 | 4.0 | 4.0 | 4.0 | 4.0 | 4.0 |
| 4. Squalene | 20.0 | 20.0 | 20.0 | 20.0 | 20.0 | 20.0 | 20.0 | 20.0 |
| 5. Decamethylcyclopentasiloxane | 14.0 | 14.0 | 14.0 | 14.0 | 14.0 | 14.0 | 0.0 | 8.0 |
| 6. Copolymer (A) of Example (1) | 6.0 |  |  |  |  |  |  |  |
| 7. Copolymer (A) of Example (3) |  | 6.0 |  |  |  |  |  |  |
| 8. Copolymer (A) of Example (6) |  |  | 6.0 |  |  |  |  |  |
| 9. Copolymer (A) of Comparative Example (1) |  |  |  | 6.0 |  |  |  |  |
| 10. Copolymer (A) of Comparative Example (3) |  |  |  |  | 6.0 |  |  |  |
| 11. Copolymer (A) of Comparative Example (6) |  |  |  |  |  | 6.0 |  |  |
| 12. Dissolved acrylic silicone copolymer (note 1) |  |  |  |  |  |  | 20.0 |  |
| 13. Silicone resin dissolution product (note 2) |  |  |  |  |  |  |  | 12.0 |
| 14. Titanium oxide | 33.0 | 33.0 | 33.0 | 33.0 | 33.0 | 33.0 | 33.0 | 33.0 |
| 15. Mica titanium | 3.0 | 3.0 | 3.0 | 3.0 | 3.0 | 3.0 | 3.0 | 3.0 |
| 16. Inorganic color pigment | 7.0 | 7.0 | 7.0 | 7.0 | 7.0 | 7.0 | 7.0 | 7.0 |
| 17. Preservative | Proper amount | Proper amount | Proper amount | Proper amount | Proper amount | Proper amount | Proper amount | Proper amount |
| 18. Perfume | Proper amount | Proper amount | Proper amount | Proper amount | Proper amount | Proper amount | Proper amount | Proper amount |

(note 1) KP-545 manufactured by Shin-Etsu Chemical Co., Ltd.
(note 2) KF-7312J manufactured by Shin-Etsu Chemical Co., Ltd.

TABLE 3

| Score | Gloss | Extension | Close | Goodness of fit | Stickiness | Moist | Finish | Make-up |
|---|---|---|---|---|---|---|---|---|
| 5 | Good | Good | Good | Good | Good | Good | Good | Good |
| 4 | Slightly good | Slightly good | Slightly good | Slightly good | Slightly good | Slightly good | Slightly good | Slightly good |
| 3 | Moderate | Moderate | Moderate | Moderate | Moderate | Moderate | Moderate | Moderate |
| 2 | Slightly bad | Slightly bad | Slightly bad | Slightly bad | Slightly bad | Slightly bad | Slightly bad | Slightly bad |
| 1 | Bad | Bad | Bad | Bad | Bad | Bad | Bad | Bad |

TABLE 4

| Grade | Average score |
|---|---|
| A | 4.5 or more |
| B | 3.5 or more and less than 4.5 |
| C | 2.5 or more and less than 3.5 |
| D | 1.0 or more and less than 2.5 |

TABLE 5

| | Example | | | Comparative Example | | | | |
|---|---|---|---|---|---|---|---|---|
| | 18 | 19 | 20 | 7 | 8 | 9 | 10 | 11 |
| Gloss | A | A | A | B | B | B | B | B |
| Extension | A | A | A | B | B | B | C | B |
| Close contact feeling | A | A | A | A | B | B | C | D |
| Goodness of fit | B | A | A | B | B | A | B | C |
| Stickiness | A | A | A | B | B | B | B | C |
| Moist feeling | A | B | A | B | B | B | C | D |
| Finish | A | A | A | B | A | B | B | B |
| Make-up retention | A | A | A | A | B | B | C | C |
| Comprehensive evaluation | A | A | A | B | B | B | C | C |

Example 21

Preparation and Evaluation of a Lipstick

A lipstick having the composition as shown in the following Table 6 was prepared, and the properties in use were evaluated. The preparation method was as follows. The obtained lipstick was very glossy on the surface of the product, and had less stickiness at the time of and after application. Also, the lipstick was excellent in adhesion feeling and free from color transfer, discoloration and blurring, and had good makeup retention.

(Preparation Method)
Step A: Components 1 to 10 were heated to dissolve.
Step B: After defoaming, components 11 and 12 were added to the mixture obtained in step A and, then, the mixture was filled in a container and molded.

TABLE 6

| Component | Example(%) 21 |
|---|---|
| 1. Microcrystalline wax | 6.0 |
| 2. Synthetic hydrocarbon wax | 8.0 |
| 3. Ceresin wax | 5.0 |
| 4. Candelilla wax | 2.0 |
| 5. Rosin acid pentaerythritol | 5.0 |
| 6. Cetyl 2-ethylhexanoate | 15.0 |
| 7. Glyceryl trioctanoate | 20.0 |
| 8. Copolymer (A) of Example (6) | 10.0 |
| 9. Methylphenyl polysiloxane | 10.0 |
| 10. Pigment | 5.0 |
| 11. Titanium mica | 15.0 |
| 12. Perfume | Proper amount |

Examples 22 to 26

Preparation and Evaluation of W/O Type Creams

W/O type creams having the compositions as shown in the following Table 7 were prepared and their properties in use were evaluated.

The preparation method was as follows.

All of the obtained W/O type creams had no oiliness and less stickiness, spread lightly and had refreshing feeling, in addition, they were excellent in adhesion feeling, are well-fitted, gave a moist and moist finish.

(Preparation Method)
Step A: Components 1 to 13 were homogeneously mixed.
Step B: Components 14 to 22 were mixed to dissolve, added to the mixture obtained in step A and stirred to be emulsified.

TABLE 7

| Component | Example(%) | | | | |
|---|---|---|---|---|---|
| | 22 | 23 | 24 | 25 | 26 |
| 1. Crosslinked alkyl polyether modified silicone (note 9) | 6.0 | | | | |
| 2. Isododecane | 13.5 | | | | |
| 3. *Macadamia* nut oil | 4.0 | 5.0 | | 3.0 | |
| 4. Crosslinked alkyl polyglycerin modified silicone (note 10) | | 7.0 | | | |
| 5. Liquid paraffin | | 13.5 | | | |
| 6. Crosslinked polyglycerin-modified silicone (note 11) | | | 7.0 | | 5.0 |
| 7. Dimethyl polysiloxane (viscosity 20 mm$^2$/s) | | | 10.0 | | 11.5 |
| 8. Crosslinked alkyl polyglycerin modified silicone (note 12) | | | | 3.0 | |
| 9. Crosslinked alkyl-modified silicone (note 13) | | | | 2.0 | |
| 10. Spherical silicone powder (note 14) | | | 3.0 | | 2.0 |

TABLE 7-continued

| Component | Example(%) | | | | |
|---|---|---|---|---|---|
| | 22 | 23 | 24 | 25 | 26 |
| 11. Alkyl polyglycerin modified silicone (note 15) | | | | 0.5 | |
| 12. Squalane | | | | 14.0 | |
| 13. The copolymer (A) of Example (10) | 1.5 | 0.5 | 0.5 | 0.5 | 0.5 |
| 14. Sodium citrate | 0.2 | 0.2 | 0.2 | 0.2 | 0.2 |
| 15. Propylene glycol | 8.0 | 8.0 | | | |
| 16. Glycerin | 3.0 | 3.0 | | 4.0 | |
| 17. Dipropylene glycol | | | | 8.0 | 10.0 |
| 18. Ethanol | | | | | 5.0 |
| 19. Sodium chloride | | | | 0.5 | 0.5 |
| 20. Preservative | Proper amount | Proper amount | Proper amount | Proper amount | |
| 21. Perfume | Proper amount | Proper amount | Proper amount | Proper amount | Proper amount |
| 22. Purified water | The rest | The rest | The rest | The rest | The rest |

(note 9)
KSG-310 manufactured by Shin-Etsu Chemical Co., Ltd.
(note 10)
KSG-810 manufactured by Shin-Etsu Chemical Co., Ltd.
(note 11)
KSG-710 manufactured by Shin-Etsu Chemical Co., Ltd.
(note 12)
KSG-840 manufactured by Shin-Etsu Chemical Co., Ltd.
(note 13)
KSG-44 manufactured by Shin-Etsu Chemical Co., Ltd.
(note 14)
KSP-100 manufactured by Shin-Etsu Chemical Co., Ltd.
(note 15)
KF-6105 manufactured by Shin-Etsu Chemical Co., Ltd.

Examples 27 and 28

Preparation and Evaluation of Suncut Creams

Suncut creams having each composition as shown in Table 8 were prepared and their properties in use were evaluated. The preparation method was as follows.

The obtained sun-cut creams had less stickiness, spread lightly, had refreshing feeling and gave good make-up retention.

(Preparation Method)

Step A: Components 1 to 11 were homogeneously mixed.

Step B: Components 12 to 15 were mixed to dissolve, added to the mixture obtained in step A and stirred to be emulsified.

TABLE 8

| Component | Example(%) | |
|---|---|---|
| | 27 | 28 |
| 1. Crosslinked polyether-modified silicone (note 16) | 2.0 | 2.0 |
| 2. Crosslinked silicone composition (note 17) | 3.0 | 3.0 |
| 3. Branched polyether-modified silicone (note 18) | 1.5 | 1.5 |
| 4. Copolymer (A) of Example (6) | 2.0 | 2.0 |
| 5. Decamethylcyclopentasiloxane | 8.3 | 8.3 |
| 6. Methyl trimethicone | | 11.3 |
| 7. Dimethyl distearyl ammonium hectorite | 1.2 | 1.2 |
| 8. Titanium oxide dispersion (note 19) | 20.0 | |
| 9. Zinc acid dispersion (note 20) | 15.0 | |
| 10. Titanium oxide dispersion (note 21) | | 17.0 |
| 11. Zinc oxide dispersion (note 22) | | 15.0 |
| 12. 1,3-butylene glycol | 5.0 | 5.0 |
| 13. Sodium citrate | 0.2 | 0.2 |
| 14. Sodium chloride | 0.5 | 0.5 |
| 15. Purified water | 41.3 | 33.0 |

(note 16)
KSG-210 manufactured by Shin-Etsu Chemical Co., Ltd.
(note 17)
KSG-15 manufactured by Shin-Etsu Chemical Co., Ltd.
(note 18)
KF-6028P manufactured by Shin-Etsu Chemical Co., Ltd.
(note 19)
SPD-T6 manufactured by Shin-Etsu Chemical Co., Ltd.
(note 20)
SPD-Z6 manufactured by Shin-Etsu Chemical Co., Ltd.
(note 21)
SPD-T3 manufactured by Shin-Etsu Chemical Co., Ltd.
(note 22)
SPD-Z3 manufactured by Shin-Etsu Chemical Co., Ltd.

Example 29

Preparation and Evaluation of a Sun-Cut Milky Lotion

A sun-cut milky lotion having the composition as shown in the following Table 9 was prepared and its properties in use were evaluated. The preparation method was as follows.

The sun-cut milky lotion obtained spread well, had less stickiness, provided refreshing make-up and good make-up retention.

(Preparation Method)

Step A: Components 1 to 6 were homogeneously mixed.

Step B: Components 9 to 12 were mixed to dissolve.

Step C: The mixture obtained in step B was added to the mixture obtained in step A and stirred to be emulsified and, then, components 7 and 8 were added to the emulsion.

TABLE 9

| Component | Example(%) 29 |
|---|---|
| 1. Crosslinked polyether-modified silicone composition (note 23) | 3.0 |
| 2. Crosslinked silicone composition (note 24) | 2.0 |
| 3. Branched polyether-modified silicone (note 25) | 1.0 |
| 4. Copolymer (A) of Example (4) | 2.0 |
| 5. Decamethylcyclopentasiloxane | 8.0 |
| 6. Isotridecyl isononanoate | 4.0 |
| 7. Titanium oxide dispersion (note 26) | 25.0 |
| 8. Zinc oxide dispersion (note 27) | 35.0 |
| 9. 1,3-butylene glycol | 2.0 |
| 10. Sodium citrate | 0.2 |
| 11. Sodium chloride | 0.5 |
| 12. Purified water | 17.3 |

(note 23) KSG-210 manufactured by Shin-Etsu Chemical Co., Ltd.
(note 24) KSG-15 manufactured by Shin-Etsu Chemical Co., Ltd.
(note 25) KF-6028P manufactured by Shin-Etsu Chemical Co., Ltd.
(note 26) SPD-T5 manufactured by Shin-Etsu Chemical Co., Ltd.
(note 27) SPD-Z5 manufactured by Shin-Etsu Chemical Co., Ltd.

Examples 30 to 32

Preparation and Evaluation of O/W Type Creams

O/W type creams having each composition as shown in the following Table 10 were prepared, and their properties in use were evaluated. The preparation method was as follows.

The O/W type creams obtained were fine, spread lightly, had less stickiness and no oiliness, were moist, gave a refreshing feeling of use and good makeup retention, had no change with temperature and time, and had excellent stability.

(Preparation Method)
Step A: Components 1 to 8 were mixed.
Step B: Components 9 to 21 were mixed to dissolve.
Step C: The mixture obtained in step A was added to the mixture obtained in step B and stirred to be emulsified.

TABLE 10

| Component | Example (%) 30 | 31 | 32 |
|---|---|---|---|
| 1. Crosslinked silicone composition (note 28) | 8.0 | 15.0 | 28.0 |
| 2. Crosslinked silicone composition (note 29) | 2.0 | | |
| 3. Isotridecyl isononanoate | 5.0 | | |
| 4. Decamethylcyclopentasiloxane | | 10.0 | 10.0 |
| 5. Crosslinked alkyl-modified silicone composition (note 30) | | 2.0 | |
| 6. Dimethyl polysiloxane (viscosity 6 mm²/s) | | 18.0 | 5.0 |
| 7. Polyglycerin-modified silicone (note 31) | | | 0.7 |
| 8. Copolymer (A) of Example (7) | 2.0 | 2.0 | 2.0 |
| 9. 1,3-butylene glycol | | | 3.0 |
| 10. Dipropylene glycol | 7.0 | 3.0 | |
| 11. Glycerin | 5.0 | | |
| 12. Methylcellulose (note 32) (2% aqueous solution) | 7.0 | | |
| 13. Polyacrylamide emulsifier (note 33) | 2.0 | 0.8 | 0.8 |
| 14. Guanine | 1.0 | | |
| 15. Xanthan gum (2% aqueous solution) | | 8.0 | |
| 16. Polyoxyethylene hardened castor oil | | | 0.5 |
| 17. Water-soluble polymer (note 34) (5% aqueous solution) | | | 10.0 |
| 18. Sodium chloride | | | 0.1 |
| 19. Preservative | Proper amount | Proper amount | Proper amount |
| 20. Perfume | Proper amount | Proper amount | Proper amount |
| 21. Purified water | The rest | The rest | The rest |

(note 28) KSG-16 manufactured by Shin-Etsu Chemical Co., Ltd.
(note 29) KSG-18 manufactured by Shin-Etsu Chemical Co., Ltd.
(note 30) KSG-43 manufactured by Shin-Etsu Chemical Co., Ltd.
(note 31) KF-6100 manufactured by Shin-Etsu Chemical Co., Ltd.
(note 32) Metroose SM 400 manufactured by Shin-Etsu Chemical Co., Ltd.
(note 33) Sepigel 305 manufactured by SEPIC
(note 34) Aristoflex AVC manufactured by Clariant Japan Co., Ltd.

Examples 33 to 35

Preparation and Evaluation of Hair Creams

Hair creams having the compositions as shown in the following Table 11 were preparation, and their properties in use were evaluated. The preparation method was as follows.

The hair cream obtained spread lightly, had less stickiness and no oiliness, was moist, gave a refreshing feeling of use, gloss, smoothness and an excellent set effect on hair.

(Preparation Method)
Step A: Components 1 to 17 were heated and mixed.
Step B: Components 18 to 27 were heated to dissolve.
Step C: The mixture obtained in step B was gradually added to the mixture obtained in step A while stirring to be emulsified, cooled, and component 28 was added thereto to obtain a hair cream.

TABLE 11

| Component | Example(%) 33 | 34 | 35 |
|---|---|---|---|
| 1. Tristrimethylsiloxypylsilane | 10.0 | | |
| 2. Methyl phenyl silicone | 5.0 | | |
| 3. Squalane | 4.0 | | |
| 4. Silicone resin dissolution product (note 35) | 1.0 | | |
| 5. Glyceryl dioleate | 2.0 | | |
| 6. Polyether modified silicone (note 36) | 2.0 | | |
| 7. Oleyl polyether modified silicone (note 37) | 4.0 | | |
| 8. Dimethyl polysiloxane (viscosity 6 mm²/s) | | | 5.0 |
| 9. Decamethylpentasiloxane | | | 8.0 |
| 10. Silicone gum dissolved product (note 38) | | 18.0 | |
| 11. Crosslinked silicone composition (note 39) | | 6.0 | |
| 12. Glyceryl tri-2-ethylhexanoate | | 8.0 | |
| 13. Vaseline | | 5.0 | |
| 14. Stearyl alcohol | | 2.0 | |
| 15. Sorbitan monooleate | | 2.0 | |
| 16. Polyglycerin-modified silicone (note 40) | | 2.0 | |
| 17. Copolymer (A) of Example (5) | 3.0 | 4.0 | 4.0 |
| 18. Preservative | Proper amount | Proper amount | Proper amount |
| 19. Sorbitol sodium sulfate | 2.0 | | |
| 20. Sodium chondroitin sulfate | 1.0 | | |
| 21. Sodium hyaluronate | 0.5 | | |
| 22. Propylene glycol | 3.0 | | 5.0 |
| 23. Purified water | The rest | The rest | The rest |
| 24. Glycerin | | 5.0 | 3.0 |
| 25. Sodium chloride | | 0.5 | |
| 26. Stearyl trimethyl ammonium chloride | | | 1.5 |

TABLE 11-continued

| Component | Example(%) | | |
|---|---|---|---|
| | 33 | 34 | 35 |
| 27. Hydroxyethyl cellulose | | | 0.2 |
| 28. Perfume | Proper amount | Proper amount | Proper amount |

(Note 35) KF-7312T manufactured by Shin-Etsu Chemical Co., Ltd.
(Note 36) KF-6017 manufactured by Shin-Etsu Chemical Co., Ltd.
(Note 37) KF-6026 manufactured by Shin-Etsu Chemical Co., Ltd.
(Note 38) MK-15H manufactured by Shin-Etsu Chemical Co., Ltd.
(Note 39) KSG-15 manufactured by Shin-Etsu Chemical Co., Ltd.
(Note 40) KF-6100 manufactured by Shin-Etsu Chemical Co., Ltd.

Examples 36 to 39

Preparation and Evaluation of a Brushing Spray, a Hair Spray, a Deodorant, and a Conditioning Mousse A brushing spray, a hair spray, a deodorant, and a conditioning mousse having each composition as shown in the following Table 12 were prepared, and their properties in use were evaluated. The preparation method was as follows.

The obtained cosmetics were used on hair, they provided shiny hair which was very smooth and was excellent in sustainability. Also, it was excellent in the dispersibility of the powder at the time of use, and it was very good with a sharp comb.

(Preparation Method)
Step A: Components 1 to 15 were mixed.
Step B: Components 16 to 24 were dissolved and homogeneously dispersed in the mixture obtained in step A. After packing in an aerosol can, the component 25 (mixture of n-butane, isobutane and propane) was charged into the can to obtain a brushing agent spray, a hair spray, a deodorant, and a conditioning mousse.

TABLE 12

| Component | Example (%) | | | |
|---|---|---|---|---|
| | Brushing agent spray 36 | Hair spray 37 | Deodorant 38 | Conditioning mousse 39 |
| 1. Isopropyl myristate | 0.8 | 5.0 | | |
| 2. Stearyl trimethyl ammonium chloride | 0.1 | | | |
| 3. Aluminum magnesium silicate | 0.1 | | | |
| 4. Lipophilic treated zinc oxide | 3.0 | | | |
| 5. Ethanol | 25.0 | | | |
| 6. Silicone treated mica | | 3.0 | | |
| 7. Chlorohydroxyaluminum | | 2.0 | | |
| 8. Isopropylmethylphenol | | 0.3 | | |
| 9. Sorbitan sesquioleate | | 0.2 | | |
| 10. Isododecane | | | 6.0 | |
| 11. Dimethyl polysiloxane (viscosity 6 mm²/s) | | | 2.0 | 2.0 |
| 12. Copolymer (A) of Example (6) | 5.0 | 5.0 | 5.0 | 5.0 |
| 13. Polyether modified silicone (note 41) | | | 0.5 | |
| 14. Crosslinked silicone composition (note 42) | | | | 0.5 |

TABLE 12-continued

| Component | Example (%) | | | |
|---|---|---|---|---|
| | Brushing agent spray 36 | Hair spray 37 | Deodorant 38 | Conditioning mousse 39 |
| 15. Glyceryl trioctanoate | | | | 1.5 |
| 16. Propylene glycol | | | 18.0 | |
| 17. Triclosan | | | 0.1 | |
| 18. Glycerin | | | 9.0 | 3.0 |
| 19. Stearyl dimethyl benzyl ammonium chloride | | | | 0.5 |
| 20. Polyoxyethylene hardened castor oil | | | | 0.5 |
| 21. Ethanol | | | | 7.0 |
| 22. Purified water | | | 29.4 | 20.0 |
| 23. Preservative | Proper amount | Proper amount | Proper amount | Proper amount |
| 24. Perfume | Proper amount | Proper amount | Proper amount | Proper amount |
| 25. Propellant | Proper amount | Proper amount | Proper amount | Proper amount |

(Note 41) KF-6017 manufactured by Shin-Etsu Chemical Co., Ltd.
(Note 42) KSG-16 manufactured by Shin-Etsu Chemical Co., Ltd.

Examples 40 and 41

Preparation and Evaluation of O/W/O Type Cosmetics

O/W/O type cosmetics having each composition as shown in the following Table 13 were prepared, and their properties in use were evaluated. The preparation method was as follows. The obtained O/W/O type cosmetics gave a refreshing feeling of use, had less stickiness and no oiliness, were transparent, gave good make-up retention, had no change in temperature or time, and were very excellent in properties in use and stability.

(Preparation Method)
Step A: Components 1 to 7 were homogeneously mixed.
Step B: Components 8 to 14 were mixed with heating and homogenized.
Step C: Components 15 to 19 were heated and mixed.
Step D: The mixture obtained in step C was added to the mixture obtained in step B while stirring to be emulsified and cooled.
Step E: The mixture obtained in step D was added to the mixture obtained in step A while stirring to be emulsified.

TABLE 13

| Component | Example(%) | |
|---|---|---|
| | Emulsion 40 | Liquid foundation 41 |
| 1. Crosslinked polyether-modified silicone (note 43) | 3.0 | 4.0 |
| 2. Polyglycerin-modified silicone (note 44) | 1.0 | 1.0 |
| 3. Glyceryl triisooctanoate | 14.0 | |
| 4. Crosslinked alkyl-modified silicone composition (note 45) | 5.0 | |
| 5. Decanoic acid propylene glycol | | 5.0 |
| 6. Isopropyl myristate | | 5.0 |
| 7. Copolymer (A) of Example (11) | 4.0 | 2.0 |
| 8. Sucrose monostearate | 3.0 | |
| 9. Glycerin | 5.0 | 2.0 |
| 10. 1,3-butylene glycol | 5.0 | 10.0 |

TABLE 13-continued

|  | Example(%) | |
|---|---|---|
| Component | Emulsion 40 | Liquid foundation 41 |
| 11. Preservative | Proper amount | Proper amount |
| 12. Purified water | 41.0 | 50.0 |
| 13. Pigment | 10.0 | 10.0 |
| 14. Egg yolk derived hydrogenated phospholipid |  | 1.0 |
| 15. Macadamia nut oil | 2.0 |  |
| 16. Cetyl alcohol | 2.0 |  |
| 17. Perfume | Proper amount | Proper amount |
| 18. Squalane | 5.0 | 5.0 |
| 19. Cetyl alcohol |  | 5.0 |

(Note 43)
KSG-210 manufactured by Shin-Etsu Chemical Co., Ltd.
(Note 44)
KF-6104 manufactured by Shin-Etsu Chemical Co., Ltd.
(Note 45)
KSG-43 manufactured by Shin-Etsu Chemical Co., Ltd.

Examples 42 and 43

Preparation and Evaluation of Antiperspirants

An antiperspirant having each composition as shown in the following Table 14 was prepared, and its properties in use were evaluated. The preparation method was as follows. The antiperspirant obtained spread lightly, had less stickiness and oiliness, did not become too white, gave a refreshing feeling of use, had no change in temperature and time, and was excellent in stability.

Preparation Method for Example 25

Step A: Components 1 to 8 were mixed.
Step B: Components 9 and 16 were added to the mixture obtained in step A and uniformly dispersed to obtain a roll-on type antiperspirant.

Preparation Method for Example 26

Step A: Components 10 to 14 were mixed.
Step B: Component 15 was dissolved in component 16.
Step C: The mixture obtained in step B was gradually added to the mixture obtained in step A while stirring to be emulsified to obtain an emulsion type antiperspirant.

TABLE 14

|  | Example(%) | |
|---|---|---|
| Component | Roll-on type 42 | Emulsification type 43 |
| 1. Crosslinked polyether-modified silicone composition (note 46) | 10.0 |  |
| 2. Dimethyl polysiloxane (viscosity 6 mm²/s) | 10.0 |  |
| 3. Crosslinked silicone composition (note 47) | 14.3 |  |
| 4. Decamethylcyclopentasiloxane | 30.0 |  |
| 5. Copolymer (A) of Example (4) | 10.5 |  |
| 6. Organically modified bentonite | 0.2 |  |
| 7. Aluminum zirconium tetrachlorohydrate |  | 20.0 |
| 8. Silicone treated zinc oxide | 5.0 |  |
| 9. Perfume | Proper amount |  |
| 10. Hexamethyldisiloxane |  | 20.0 |
| 11. Isododecane |  | 10.0 |
| 12. Copolymer (A) of Example (6) |  | 2.0 |
| 13. Oleyl polyether modified silicone (note 48) |  | 1.0 |
| 14. POE monooleate (20 mol) sorbitan |  | 0.5 |
| 15. Glycine salt of aluminum zirconium tetrachloride hydrate |  | 20.0 |
| 16. Purified water |  | The rest |

(Note 46)
KSG-210 manufactured by Shin-Etsu Chemical Co., Ltd.
(Note 47)
KSG-15 manufactured by Shin-Etsu Chemical Co., Ltd.
(Note 48)
KF-6026 manufactured by Shin-Etsu Chemical Co., Ltd.

Examples 44 to 48

Preparation and Evaluation of Cleansing Agents

Various cleansing agents having the each composition as shown in the following Table 15 were prepared and their properties in use were evaluated. The preparation method was as follows. The cleansing agents obtained were quick to familiar with lipstick, foundation dirt and hair setting agents, had excellent effect of washing out stain, spread well at the time of application, provided the moist skin and had a very good feeling.

(Preparation Method)
Step A: Components 1 to 4 were homogeneously dissolved.
Step B: Components 5 to 21 were homogeneously dissolved.
Step C: The mixture obtained in step A was added to the mixture obtained in step B while stirring and homogeneously dispersed.

TABLE 15

|  | Example(%) | | | | |
|---|---|---|---|---|---|
| Component | Cleansing agent 44 | Facial wash 45 | Make-up remover 46 | Hair make-up remover 47 | Facial wash 48 |
| 1. Tetrakistrimethyl-siloxysilane |  |  | 20.0 |  | 5.0 |
| 2. Isododecane |  |  |  | 20.0 |  |
| 3. Copolymer (A) of Example (6) | 2.0 | 5.0 | 1.0 | 5.0 | 5.0 |
| 4. Decamethylcyclopentasiloxane | 10.0 | 10.0 |  |  |  |
| 5. POE (10 mol) sorbitan monolaurate | 30.0 | 5.0 | 10.0 |  |  |
| 6. POE (15 mel) isocetyl ether |  |  |  | 10.0 |  |
| 7. POE (6 mol) lauryl ether |  |  |  |  | 5.0 |
| 8. Sodium chloride | 1.0 |  |  | 0.5 |  |
| 9. Polyether modified silicone (note 49) | 18.0 | 15.0 |  |  |  |
| 10. Ethanol |  | 10.0 |  |  | 10.0 |
| 11. Glycerin |  | 2.0 | 5.0 | 10.0 |  |
| 12. Lauryl-dimethylamine oxide |  |  |  |  | 2.0 |
| 13. Dipropylene glycol |  | 3.0 |  |  | 3.0 |
| 14. 1,3-butylene glycol |  |  |  | 10.0 |  |
| 15. Sodium glutamate |  | 0.5 |  |  |  |
| 16. Sorbitol |  |  | 10.0 |  |  |
| 17. Carrageenan |  |  |  | 0.5 | 0.5 |

TABLE 15-continued

| Component | Cleansing agent 44 | Facial wash 45 | Make-up remover 46 | Hair make-up remover 47 | Facial wash 48 |
|---|---|---|---|---|---|
| 18. Preservative | Proper amount | Proper amount | Proper amount | Proper amount | Proper amount |
| 19. Sodium citrate | | | 0.5 | | |
| 20. Purified water | The rest | The rest | The rest | The rest | The rest |
| 21. Perfume | Proper amount | Proper amount | Proper amount | Proper amount | Proper amount |

(Note 49)
KF-6011 manufactured by Shin-Etsu Chemical Co., Ltd.

Example 49

Preparation and Evaluation of a W/O Cheek

A W/O cheek having the composition as shown in the following Table 16 was prepared, and its properties in use were evaluated. The preparation method was as follows. The obtained W/O cheek lightly spread, had no sticky feeling and no oily feeling, gave moist and stable make-up after applying on the skin.

(Preparation Method)
Step A: Components 1 to 11 were homogeneously mixed.
Step B: Components 12 to 14 were homogeneously mixed.
Step C: The mixture obtained in step B was added to the mixture obtained in step A while stirring to be homogeneously emulsified.

TABLE 16

| Component | Example(%) 49 |
|---|---|
| 1. Acrylic silicone copolymer dissolution product (note 50) | 7.5 |
| 2. Stearyl modified acrylic silicone copolymer (note 51) | 2.0 |
| 3. Branched polyether-modified silicone (note 52) | 1.5 |
| 4. Dimethyl polysiloxane (viscosity 2 mm$^2$/s) | 21.0 |
| 5. Glyceryl triisostearate | 3.0 |
| 6. Copolymer (A) of Example (3) | 1.5 |
| 7. Dimethyl distearyl ammonium hectorite | 1.5 |
| 8. Spherical nylon | 3.0 |
| 9. Talc | 4.0 |
| 10. Cheek red pigment (acrylic silicone treatment) (note 53) | 20.0 |
| 11. Alcohol | 5.0 |
| 12. Perfume | Proper amount |
| 13. Purified water | 30.0 |
| 14. 1,3-butylene glycol | The rest |

(Note 50)
KP-574L manufactured by Shin-Etsu Chemical Co., Ltd.
(Note 51)
KF-6013 manufactured by Shin-Etsu Chemical Co., Ltd.
(Note 52)
KF-6028P manufactured by Shin-Etsu Chemical Co., Ltd.
(Note 53)
Treated with KP-574 manufactured by Shin-Etsu Chemical Co., Ltd.

Examples 50 to 52

Preparation and Evaluation of Eye Shadows

Eye shadows having each composition as shown in Table 17 were prepared and their properties in use were evaluated. The preparation method was as follows. The eye shadow obtained lightly spread, had no oiliness and powderiness, was fresh, gave a refreshing feeling of use, had good in water resistance, water repellency, good perspiration resistance and well-being, gave make-up retention, and had no change in temperature and time and stability.

(Preparation Method)
Step A: Components 1 to 10 were mixed, components 11 to 19 are added and dispersed homogeneously.
Step B: Components 20 to 26 were dissolved homogeneously.
Step C: The mixture obtained in step B was gradually added to the mixture obtained in step A while stirring to be emulsified to obtain an eye shadow.

TABLE 17

| Component | Example(%) 50 | 51 | 52 |
|---|---|---|---|
| 1. Decamethylcyclopentasiloxane | 15.0 | | |
| 2. Dimethyl polysiloxane (viscosity 6 mm$^2$/s) | 10.0 | | 4.0 |
| 3. Copolymer (A) of Example (13) | 5.0 | 5.0 | 5.0 |
| 4. Both terminals polyether-modified silicone (note 54) | 2.0 | | |
| 5. PEG (10) lauryl ether | 0.5 | | |
| 6. Acrylic silicone copolymer dissolved product (note 55) | | 10.0 | |
| 7. Stearyl modified acrylic silicone copolymer (note 56) | | 2.0 | |
| 8. Polyether modified silicone (note 57) | | 1.5 | |
| 9. Organically modified clay mineral (note 58) | | 1.2 | |
| 10. Cetyl isooctanoate | | 3.0 | |
| 11. Silicone treated chromium oxide | 6.2 | 6.5 | 5.0 |
| 12. Silicone treated ultramarine blue | 4.0 | 4.0 | 4.0 |
| 13. Silicone treated titanium coated mica | 6.0 | 6.0 | 5.0 |
| 14. Nylon powder | | 3.0 | |
| 15. Talc | | 4.0 | The rest |
| 16. Sericite | | | 40.0 |
| 17. Mica | | | 10.0 |
| 18. Particulate titanium oxide | | | 15.0 |
| 19. Magnesium stearate | | | 3.0 |
| 20. Octyldodecanol | | | 3.0 |
| 21. Sodium chloride | 2.0 | | |
| 22. Propylene glycol | 8.0 | | |
| 23. Preservative | Proper amount | Proper amount | |
| 24. Perfume | Proper amount | Proper amount | |
| 25. Purified water | The rest | The rest | |
| 26. Ethanol | | 5.0 | |

(Note 54)
KF-6009 manufactured by Shin-Etsu Chemical Co., Ltd.
(Note 55)
KP-550 manufactured by Shin-Etsu Chemical Co., Ltd.
(Note 56)
KP-561P manufactured by Shin-Etsu Chemical Co., Ltd.
(Note 57)
KF-6104 manufactured by Shin-Etsu Chemical Co., Ltd.
(Note 58)
Benton 38 manufactured by NL Industries, Inc.
(Note 59)
Treated with KF-9909 manufactured by Shin-Etsu Chemical Co., Ltd.

Examples 53 to 55

Preparation and Evaluation of Various Cosmetics

Various cosmetics having each composition as shown in the following Table 18 were prepared, and their properties in use were evaluated. The preparation method was as follows. The cosmetics obtained lightly spread, had fresh and less stickiness, no change in temperature and time, and were very excellent in properties in use and stability.

(Preparation Method)
Step A: Components 1 to 11 were homogeneously mixed.
Step B: Components 12 to 20 were homogeneously dissolved.

Step C: The mixture obtained in step B was gradually added to the mixture obtained in step A with stirring to be emulsified, cooled and Component 21 was added thereto to obtain a cosmetic.

TABLE 18

| Component | Example(%) | | |
|---|---|---|---|
| | Emulsion 53 | Liquid foundation 54 | Rinse-off type pack 55 |
| 1. Dimethyl polysiloxane (viscosity 2 mm$^2$/s) | 12.0 | | |
| 2. Glyceryl triisooctanoate | 10.0 | 3.0 | |
| 3. Dimethyl polysiloxane (viscosity 5 mm$^2$/s) | | | 3.0 |
| 4. Polyether modified silicone (note 59) | 0.2 | | |
| 5. Crosslinked polyether-modified silicone composition (note 60) | 2.0 | | |
| 6. Copolymer (A) of Example (1) | 2.0 | 5.0 | 3.0 |
| 7. Ethanol | | 15.0 | |
| 8. Polyether modified silicone (note 61) | | 0.5 | 2.0 |
| 9. Stearoxy modified silicone (note 62) | | 2.0 | |
| 10. Spherical silicone powder (63) | | 8.0 | |
| 11. Kaolin | | | 30.0 |
| 12. Glycerin | 10.0 | | 10.0 |
| 13. Ascorbic acid phosphate magnesium salt | 3.0 | | |
| 14. Polyether modified silicone (note 64) | 1.0 | 1.0 | 1.0 |
| 15. Sodium chloride | 2.0 | | |
| 16. Preservative | Proper amount | Proper amount | Proper amount |
| 17. Purified water | The rest | The rest | The rest |
| 18. Carboxyvinyl polymer (1% aqueous solution) | | 20.0 | 20.0 |
| 19. Triethanolamine | | 0.2 | 0.2 |
| 20. 1,3-butylene glycol | | | 10.0 |
| 21. Perfume | Proper amount | Proper amount | Proper amount |

(Note 59)
KF-6017 manufactured by Shin-Etsu Chemical Co., Ltd.
(Note 60)
KSG-21 manufactured by Shin-Etsu Chemical Co., Ltd.
(Note 61)
KF-6018 manufactured by Shin-Etsu Chemical Co., Ltd.
(Note 62)
KF-7002 manufactured by Shin-Etsu Chemical Co., Ltd.
(Note 63)
KSP-100 manufactured by Shin-Etsu Chemical Co., Ltd.
(Note 64)
KF-6043 manufactured by Shin-Etsu Chemical Co., Ltd.

Examples 56 to 59

Preparation and Evaluation of Various Cosmetics

Various cosmetics having each composition as shown in the following Table 19 were prepared, and their properties in use were evaluated. The preparation method was as follows. The cosmetics obtained became a cosmetic which had less stickiness, lightly spread, and gave an excellent in adhesion feeling, well-fitting and glossy finish.

(Preparation Method)
Step A: Components 16 to 25 were homogeneously dispersed.
Step B: Components 1 to 15 and 26 were homogeneously mixed and added to the mixture obtained in step A and homogeneously stirred.
Step C: Component 27 was added to the mixture obtained in step B, filled it in a container (press molding as needed) to obtain a cosmetic.

TABLE 19

| Component | Example(%) | | | |
|---|---|---|---|---|
| | Powder foundation 56 | Powder eyebrow 57 | Oily foundation 58 | Mascara 59 |
| 1. Vaseline | 2.5 | 2.5 | | |
| 2. Squalane | 3 | | | |
| 3. Dimethyl polysiloxane (viscosity 6 mm$^2$/s) | | 1.5 | | |
| 4. Methyl trimethicone | | | 14 | |
| 5. Behenyl-modified acrylic silicone copolymer (note 65) | | | | 10 |
| 6. Tristrimethyl-siloxypropylsilane | | | | 10 |
| 7. Dextrin fatty acid ester (note 66) | | | 6 | 8 |
| 8. Ceresin | | | 7 | 7 |
| 9. Polyethylene wax | | | | 4 |
| 10. Lecithin | | | | 0.5 |
| 11. Isododecane | | | | 20 |
| 12. Copolymer (A) of Example (2) | 0.5 | 0.5 | 4 | 4 |
| 13. Glyceryl trioctanoate | 2 | 4 | | |
| 14. Liquid paraffin | | | 20 | 18 |
| 15. Alkyl polyglycerin modified silicone (note 67) | | | 6 | |
| 16. Silicone treatment (note 68) Mica | 40 | 41 | 10 | |
| 17. Silicone treatment (note 68) Talc | The rest | The rest | | The rest |
| 19. Silicone treatment (note 68) Titanium oxide fine particles | 5 | 10 | The rest | |
| 20. Silicone treatment (note 68) Barium sulfate | 10 | 15 | | |
| 20. Silicone treatment (note 68) Iron oxide | | | | 5 |
| 21. Hydrophohicized silica (note 69) | | | | 3.5 |
| 22. Titanium mica | | | 3 | |
| 23. Spherical silicone powder (note 70) | 2 | | | |
| 24. Spherical silicone powder (note 71) | | 1.5 | | |
| 25. Spherical silicone powder (note 72) | 2.5 | 2.5 | | |
| 26. Preservative | Proper amount | Proper amount | Proper amount | |
| 27. Perfume | Proper amount | Proper amount | Proper amount | |

(Note 65)
KP-562P manufactured by Shin-Etsu Chemical Co., Ltd.
(Note 66)
Leopard TT manufactured by Chiba Flour Milling Co.
(Note 67)
KF-9909 manufactured by Shin-Etsu Chemical Co., Ltd.
(Note 68)
AEROSIL RY 200 manufactured by Nippon Aerosil Co., Ltd.
(Note 69)
KF-6105 manufactured by Shin-Etsu Chemical Co., Ltd.
(Note 70)
KSP-300 manufactured by Shin-Etsu Chemical Co., Ltd.
(Note 71)
KSP-100 manufactured by Shin-Etsu Chemical Co., Ltd.
(Note 72)
KMP-590 manufactured by Shin-Etsu Chemical Co., Ltd.

Examples 60 to 62

Preparation and Evaluation of Eyeliners

Eyeliners having each composition as shown in the following Table 20 were prepared, and their properties in use was evaluated. The preparation method was as follows.

The eyeliners obtained lightly spread, were easy to draw, had refreshing feeling, had refresh feeling with less stickiness, no change in temperature and time, good properties in use and stability, excellent water resistance and perspiration resistance, and provided the good make-up retention.

(Preparation Method)

Step A: Components 1 to 11 were mixed to homogeneously disperse.

Step B: Components 12 to 16 were mixed.

Step C: The mixture obtained in step B was gradually added to the mixture obtained in step A to be emulsified, and then cooled to obtain an eyeliner.

TABLE 20

| Component | Example (%) | | |
|---|---|---|---|
| | 60 | 61 | 62 |
| 1. Methyl trimethicone | 53.5 | | |
| 2. Tristrimethylsiloxypropylsilane | | 20.0 | |
| 3. Dimethyl polysiloxane (viscosity 6 mm²/s) | | 5.0 | 5.0 |
| 4. Polyether modified silicone (note 73) | 3.0 | | 1.0 |
| 5. Silicone resin dissolution product (note 74) | 5.0 | | |
| 6. Vitamin E acetate | | 0.2 | |
| 7. Jojoba oil | | 2.0 | 2.0 |
| 8. Bentonite | | 3.0 | |
| 9. Copolymer (A) of Example (3) | 10.0 | 2.0 | 22.0 |
| 10. Dimethyl distearyl ammonium hectorite | 3.0 | | |
| 11. Silicone treatment (note 75) Black iron oxide | 10.0 | 20.0 | 20.0 |
| 12. Ethanol | | 10.0 | 5.0 |
| 13. 1,3-butylene glycol | 5.0 | 10.0 | |
| 14. Sodium sulfate | 0.5 | | |
| 15. Preservative | Proper amount | Proper amount | Proper amount |
| 16. Purified water | The rest | The rest | The rest |

(Note 73)
KF-6017 manufactured by Shin-Etsu Chemical Co., Ltd.
(Note 74)
KF-7312T manufactured by Shin-Etsu Chemical Co., Ltd.
(Note 75)
Hydrophobic treatment: 2% of methylhydrogenpolysiloxane, relative to the amount of the Black iron oxide powder, was added to the Black iron oxide powder and heated so as to treat the Black iron oxide.

Examples 63 to 66

Preparation and Evaluation of Various Cosmetics

Various cosmetics having each composition as shown in the following Table 21 were prepared, and their properties in use was evaluated. The preparation method was as follows. The cosmetics obtained had fine texture, lightly spread, had less stickiness and no oily feeling, were moist, gave a refreshing feeling of use and good makeup retention, and had no change in temperature and time and excellent stability.

(Preparation Method)

Step A: Components 1 to 8 were heated and mixed.

Step B: Components 9 to 19 were heated to dissolve.

Step C: The mixture obtained in step B was gradually added to the mixture obtained in step A and homogeneously dispersed while stirring, and component 20 was added thereto to obtain a cosmetic.

TABLE 21

| Component | Example(%) | | | |
|---|---|---|---|---|
| | Transparent gel cosmetic 63 | Anti-perspirant 64 | Anti-perspirant 65 | After-shave cream 66 |
| 1. Polyglycerin-modified silicone (note 76) | 10.0 | | | |
| 2. Decamethylcyclopentasiloxane | | 30.0 | 30.0 | 35.0 |
| 3. Polyoxyethylene sorbitan monooleate (20 EO) | | | 0.5 | |
| 4. Aloe extract | | | | 0.1 |
| 5. Crosslinked polyether-modified silicone (note 77) | | 20.0 | | |
| 6. Crosslinked silicone composition (note 78) | | 20.0 | | |
| 7. Polyether modified silicone (note 79) | | | | 2.9 |
| 8. Copolymer (A) of Example (4) | 10.0 | 10.0 | 5.0 | 5.0 |
| 9. 1,3-butylene glycol | 10.0 | | | |
| 10. Polyethylene glycol 400 | 9.0 | | | 5.0 |
| 11. 2-Hydroxyoctanoic acid | 1.0 | | | |
| 12. 70% sorbitol | 10.0 | | | |
| 13. Cuninic acid | Reasonable amount | | | |
| 14. Cuninic acid sodium salt | Reasonable amount | | | |
| 15. Aluminum Zirconiumu Tetrachlorohydrex GLY | | 20.0 | 20.0 | |
| 16. Sodium L-glutamate | | | | 2.0 |
| 17. Purified water | Proper amount | The rest | The rest | |
| 18. Preservative | Proper amount | Proper amount | Proper amount | |
| 19. Perfume | Proper amount | Proper amount | Proper amount | |

(Note 76)
KF-6100 manufactured by Shin-Etsu Chemical Co., Ltd.
(Note 77)
KSG-15 manufactured by Shin-Etsu Chemical Co., Ltd.
(Note 78)
KSG-210 manufactured by Shin-Etsu Chemical Co., Ltd.
(Note 79)
KF-6017 manufactured by Shin-Etsu Chemical Co., Ltd.

Example 67

Preparation and Evaluation of a Transparent Cleansing Lotion

A transparent cleansing lotion having the composition as shown in the following Table 22, and its properties in use were evaluated. The preparation method was as follows. The transparent cleansing lotion obtained lightly spread, had moist feeling and gave high cleansing effect.

(Preparation Method)

Step A: Components 1 to 4 were homogeneously mixed.

Step B: Components 4 to 10 were homogeneously mixed.

Step C: The mixture obtained in step A was gradually added to the mixture obtained in step B while stirring to be emulsified to obtain a transparent cleansing lotion.

TABLE 22

| Component | Example(%) 67 |
|---|---|
| 1. Decamethylcyclopentasiloxane | 53.8 |
| 2. Copolymer (A) of Example (5) | 2.0 |
| 3. Neopentyl glycol dioctanoate | 6.0 |
| 4. Silica | 0.2 |
| 5. 1,3-butylene glycol | 5.0 |

TABLE 22-continued

| Component | Example(%) 67 |
|---|---|
| 6. Glycerin | 6.0 |
| 7. Polyether modified silicone (note 80) | 5.0 |
| 8. Polyether-modified silicone (note 81) | 3.0 |
| 9. PEG-60 hydrogenated castor oil | 2.0 |
| 10. Purified water | 17.0 |

(Note 80)
KF-6011 manufactured by Shin-Etsu Chemical Co., Ltd.
(Note 81)
KF-6013 manufactured by Shin-Etsu Chemical Co., Ltd.

Example 68

Preparation and Evaluation of a Cuticle Coat

A cuticle coat having the composition as shown in the following Table 23 was prepared, and its properties in use was evaluated. The preparation method was as follows. The cuticle coat obtained lightly spread, suppresses dry feeling of hair and gave gloss and smoothness on hair.
(Preparation Method)
Step A: Components 1 to 3 were homogeneously mixed.
Step B: Components 4 to 10 were homogeneously mixed.
Step C: The mixture obtained in step A was gradually added to the mixture obtained in step B while stirring to be emulsified to obtain a cuticle coat.

TABLE 23

| Component | Example(%) 68 |
|---|---|
| 1. Copolymer (A) of Example (6) | 1.0 |
| 2. Silicone gum dissolved product (note 82) | 40.0 |
| 3. Decamethylcyclopentasiloxane | 42.0 |
| 4. Polyether-modified silicone (note 83) | 3.0 |
| 5. Polyether modified silicone (note 84) | 2.0 |
| 6. PEG-40 hydrogenated cured castor oil | 1.0 |
| 7. Alcohol | 5.0 |
| 8. Preservative | Proper amount |
| 9. Perfume | Proper amount |
| 10. Purified water | 6.0 |

(Note 82)
KF-9028 manufactured by Shin-Etsu Chemical Co., Ltd.
(Note 83)
KF-6011 manufactured by Shin-Etsu Chemical Co., Ltd.
(Note 84)
KF-6013 manufactured by Shin-Etsu Chemical Co., Ltd.

Example 69

Preparation and Evaluation of a Nail Enamel

Nail enamel having the composition as shown in the following Table 24 was prepared, and its properties in use were evaluated. The preparation method was as follows. The Nail enamel obtained lightly spread and gave glossy on nails and had excellent retention.
(Preparation Method)
Step A: Component 2, a part of Component 5, and Component 10 were mixed.
Step B: A part of Component 1, a part of Component 8 and Component 9 were mixed and thoroughly kneaded.
Step C: The rest of Component 1, Components 3 and 4, the rest of Component 5, Components 6 and 7, and the rest of Component 8 were mixed to dissolve homogeneously.

Step D: The mixtures obtained in steps A, B and C were mixed to be an uniform cosmetic.

TABLE 24

| Component | Example(%) 69 |
|---|---|
| 1. Nitrocellulose | 10.0 |
| 2. Modified alkyd resin | 12.0 |
| 3. Toluene sulfonamide resin | 5.0 |
| 4. Copolymer (A) of Example (6) | 11.0 |
| 5. Acetyl tributyl citrate | 5.0 |
| 6. Butyl acetate | 35.0 |
| 7. Ethyl acetate | 17.0 |
| 8. Isopropanol | 5.0 |
| 9. Organically modified bentonite | Proper amount |
| 10. Pigment | Proper amount |

As described above, the cosmetic which does not comprise the present copolymer is inferior in feeling in use and cosmetic retention (as seen in Comparative Examples). In contrast, as shown in Examples, the cosmetic comprising the present copolymer has good compatibility with various oily agents and gives good adhesion to skin or hair. Therefore, the cosmetic of the present invention has less stickiness, spread smoothly, gives refreshing feeling in use, excellent water repellency, highly safe for skin, good properties in use and excellent sustainability. Therefore, the present copolymer is suitably used for various cosmetics such as skin care cosmetics, make-up cosmetics, hair cosmetics, and ultraviolet protective cosmetics.

The invention claimed is:
1. A method for preparing a (meth)acrylic silicone graft (co)polymer having a unit represented by the following formula (I), a structure represented by the following formula (III) at one terminal, and a structure represented by the following formula (IV) at the other terminal,

(III)

(I)

(IV)

wherein $R^1$ is, independently of each other, a hydrogen atom or a methyl group, $R^7$ is an alkyl group having 1 to 4 carbon atoms, $R^8$ and $R^9$ are, independently of each other, a hydrogen atom or an alkyl group having 1 to 4 carbon atoms, $R^{10}$ is a hydrogen atom or a methyl group, A is a group having a linear organopolysiloxane structure represented by the following formula (1) or a group having a dendritic organopolysiloxane structure represented by the following formula (2-1) or (2-2), X' is a group as defined for A, and p is an integer such that the (co)polymer has a number average molecular weight of 1,000 to 1,000,000 g/mol,

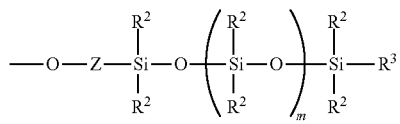 (1)

wherein Z is a divalent organic group, $R^2$ is a saturated hydrocarbon group having 1 to 10 carbon atoms or a phenyl group, $R^3$ is a saturated hydrocarbon group having 1 to 10 carbon atoms, and m is an integer of from 0 to 100,

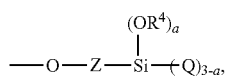 (2-1)

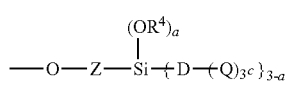 (2-2)

wherein Z is a divalent organic group, a is a number of 0 to 3, Q is a group represented by the following formula (2), D is a $(3^c+1)$-valent organopolysiloxanyl group which has a hierachial order of c, $3^c$ means 3 raised to the power of c, c is an integer of from 1 to 8,

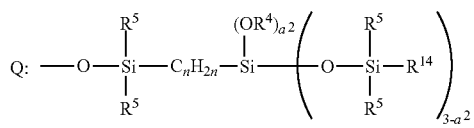 (2)

wherein $R^4$ is a saturated hydrocarbon group having 1 to 10 carbon atoms or a phenyl group, $R^5$ is a saturated hydrocarbon group having 1 to 6 carbon atoms or a phenyl group, $R^{14}$ is a hydrogen atom, a saturated hydrocarbon group having 1 to 10 carbon atoms or a phenyl group $a^2$ is the number of 0 to 2, and n is an integer of from 2 to 12, wherein the method comprises a step of group transfer polymerization of a compound represented by the following general formula (4),

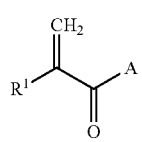 (4)

wherein $R^1$ and A are as defined above, in the presence of a compound represented by the following general formula (6) as an initiator

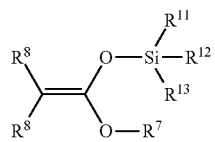 (6)

wherein $R^7$, $R^8$ and $R^9$ are as defined above, $R^{11}$, $R^{12}$ and $R^{13}$ are, independently of each other, an alkyl group having 1 to 4 carbon atoms, and further comprises a step of distilling off the monomer represented by the aforesaid formula (4) under a reduced pressure at a temperature of 100 degrees C. or higher after the group transfer polymerization.

2. A method for preparing a (meth)acrylic silicone graft copolymer having a unit represented by the following formula (I), a unit represented by the following formula (II), a structure represented by the following formula (III) at one terminal and a structure represented by the following formula (IV) at the other terminal,

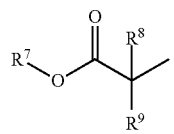 (III)

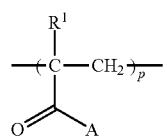 (I)

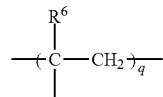 (II)

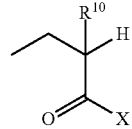 (IV)

wherein $R^1$ and $R^6$ are, independently of each other, a hydrogen atom or a methyl group, $R^7$ is an alkyl group having 1 to 4 carbon atoms, $R^8$ and $R^9$ are, independently of each other, a hydrogen atom or an alkyl group having 1 to 4 carbon atoms, $R^{10}$ is a hydrogen atom or a methyl group, B is an alkoxy group which has 1 to 20 carbon atoms, an aryloxy group having 6 to 20 carbon atoms, an amino group, a siloxy group, a halogen atom, a hydroxyl group or a substituted or unsubstituted, monovalent hydrocarbon group which has 1 to 20 carbon atoms and may have at least one selected from —O—, —S— and —NR—, wherein R is a hydrogen atom or a monovalent hydrocarbon group having 1 to 20 carbon atoms, provided that the oxygen atom, the sulfur atom and the nitrogen atom are not adjacent to each other, and A is a group having a linear organopolysiloxane structure represented by the following formula (1) or a group having a dendritic organopolysiloxane structure represented by the following formula (2-1) or (2-2), X is a group as defined for A or B, an order of the units (I) and (II) is not limited, p is an integer of 1 or larger, q is an integer of 1 or larger, and p+q is the number such that the copolymer has a number average molecular weight of 1,000 to 1,000,000 g/mol,

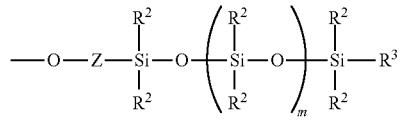 (1)

wherein Z is a divalent organic group, $R^2$ is a saturated hydrocarbon group having 1 to 10 carbon atoms or a phenyl group, $R^3$ is a saturated hydrocarbon group having 1 to 10 carbon atoms, and m is an integer of from 0 to 100,

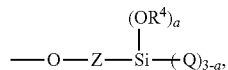 (2-1)

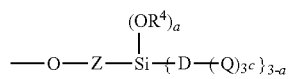 (2-2)

wherein Z is a divalent organic group, a is a number of 0 to 3, Q is a group represented by the following formula (2), D is a $(3^c+1)$-valent organopolysiloxanyl group which has a hierachial order of c, $3^c$ means 3 raised to the power of c, c is an integer of from 1 to 8,

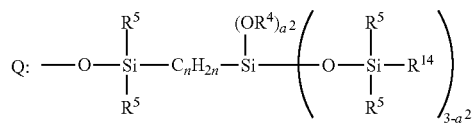 (2)

wherein $R^4$ is a saturated hydrocarbon group having 1 to 10 carbon atoms or a phenyl group, $R^5$ is a saturated hydrocarbon group having 1 to 6 carbon atoms or a phenyl group, $R^{14}$ is a hydrogen atom, a saturated hydrocarbon group having 1 to 10 carbon atoms or a phenyl group, $a^2$ is the number of 0 to 2, and n is an integer of from 2 to 12, wherein the method comprises a step of group transfer polymerization of a compound represented by the following general formula (4) and a compound represented by the following general formula (5),

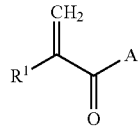 (4)

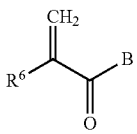 (5)

wherein $R^1$, $R^6$, A and B are as defined above, in the presence of a compound represented by the following general formula (6) as an initiator

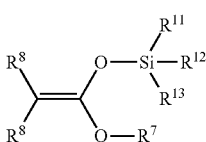 (6)

wherein $R^7$, $R^8$ and $R^9$ are as defined above, $R^{11}$, $R^{12}$ and $R^{13}$ are, independently of each other, an alkyl group having 1 to 4 carbon atoms, and further comprises a step of distilling off the monomers represented by the aforesaid formula (4) or (5) under a reduced pressure at a temperature of 100 degrees C. or higher after the group transfer polymerization.

3. A cosmetic comprising a (meth)acrylic silicone graft (co)polymer having a unit represented by the following formula (I), a structure represented by the following formula (III) at one terminal, and a structure represented by the following formula (IV) at the other terminal,

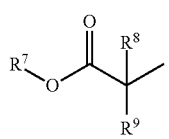 (III)

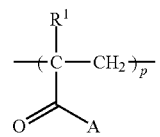 (I)

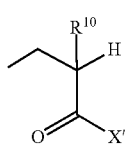 (IV)

wherein $R^1$ is, independently of each other, a hydrogen atom or a methyl group, $R^7$ is an alkyl group having 1 to 4 carbon atoms, $R^8$ and $R^9$ are, independently of each other, a hydrogen atom or an alkyl group having 1 to 4 carbon atoms, $R^{10}$ is a hydrogen atom or a methyl group, A is a group having a linear organopolysiloxane structure represented by the following formula (1) or a group having a dendritic organopolysiloxane structure represented by the following formula (2-1) or (2-2), X' is a group as defined for A, and p is an integer such that the (co)polymer has a number average molecular weight of 1,000 to 1,000,000 g/mol,

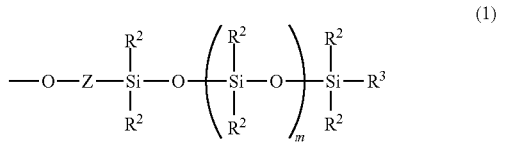

(1)

wherein Z is a divalent organic group, R² is a saturated hydrocarbon group having 1 to 10 carbon atoms or a phenyl group, R³ is a saturated hydrocarbon group having 1 to 10 carbon atoms, and m is an integer of from 0 to 100,

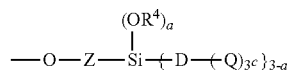

(2-1)

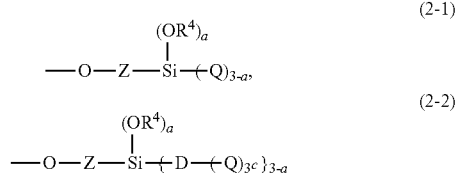

(2-2)

wherein Z is a divalent organic group, a is a number of 0 to 3, Q is a group represented by the following formula (2), D is a $(3^c+1)$-valent organopolysiloxanyl group which has a hierachial order of c, $3^c$ means 3 raised to the power of c, c is an integer of from 1 to 8,

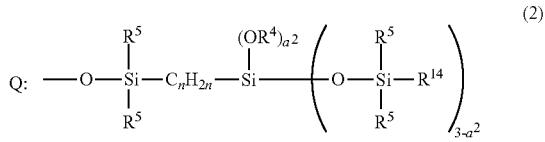

(2)

wherein R⁴ is a saturated hydrocarbon group having 1 to 10 carbon atoms or a phenyl group, R⁵ is a saturated hydrocarbon group having 1 to 6 carbon atoms or a phenyl group, R¹⁴ is a hydrogen atom, a saturated hydrocarbon group having 1 to 10 carbon atoms or a phenyl group, a² is the number of 0 to 2, and n is an integer of from 2 to 12.

4. A cosmetic comprising a (meth)acrylic silicone graft copolymer having a unit represented by the following formula (I), a unit represented by the following formula (II), a structure represented by the following formula (III) at one terminal and a structure represented by the following formula (IV) at the other terminal,

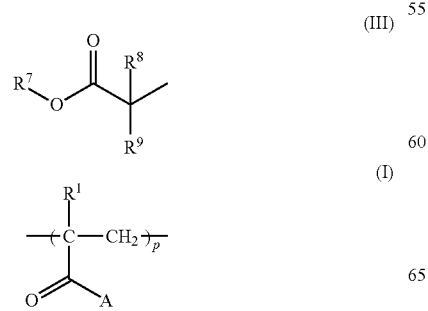

(III)

(I)

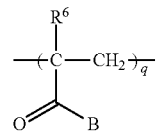

(II)

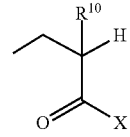

(IV)

wherein R¹ and R⁶ are, independently of each other, a hydrogen atom or a methyl group, R⁷ is an alkyl group having 1 to 4 carbon atoms, R⁸ and R⁹ are, independently of each other, a hydrogen atom or an alkyl group having 1 to 4 carbon atoms, R¹⁰ is a hydrogen atom or a methyl group, B is an alkoxy group which has 1 to 20 carbon atoms, an aryloxy group having 6 to 20 carbon atoms, an amino group, a siloxy group, a halogen atom, a hydroxyl group or a substituted or unsubstituted, monovalent hydrocarbon group which has 1 to 20 carbon atoms and may have at least one selected from —O—, —S— and —NR—, wherein R is a hydrogen atom or a monovalent hydrocarbon group having 1 to 20 carbon atoms, provided that the oxygen atom, the sulfur atom and the nitrogen atom are not adjacent to each other, and A is a group having a linear organopolysiloxane structure represented by the following formula (1) or a group having a dendritic organopolysiloxane structure represented by the following formula (2-1) or (2-2), X is a group as defined for A or B, an order of the units (I) and (II) is not limited, p is an integer of 1 or larger, q is an integer of 1 or larger, and p+q is the number such that the copolymer has a number average molecular weight of 1,000 to 1,000,000 g/mol,

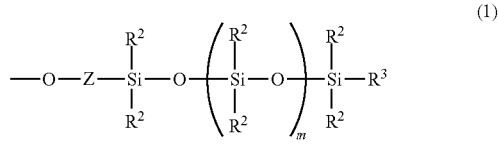

(1)

wherein Z is a divalent organic group, R² is a saturated hydrocarbon group having 1 to 10 carbon atoms or a phenyl group, R³ is a saturated hydrocarbon group having 1 to 10 carbon atoms, and m is an integer of from 0 to 100,

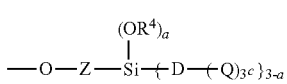

(2-1)

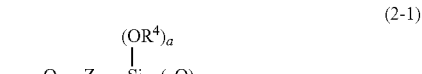

(2-2)

wherein Z is a divalent organic group, a is a number of 0 to 3, Q is a group represented by the following formula (2), D is a $(3^c+1)$-valent organopolysiloxanyl group which has a hierachial order of c, $3^c$ means 3 raised to the power of c, c is an integer of from 1 to 8,

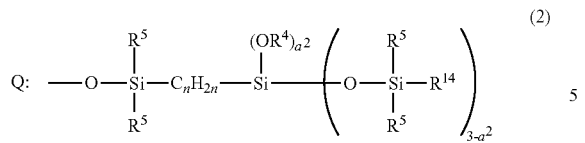

wherein $R^4$ is a saturated hydrocarbon group having 1 to 10 carbon atoms or a phenyl group $R^5$ is a saturated hydrocarbon group having 1 to 6 carbon atoms or a phenyl group, $R^{14}$ is a hydrogen atom, a saturated hydrocarbon group having 1 to 10 carbon atoms or a phenyl group, $a^2$ is the number of 0 to 2, and n is an integer of from 2 to 12.

5. The cosmetic according to claim 3, wherein a temperature at which loss of the weight of the (co)polymer is 50% in a nitrogen atmosphere is 360 degrees C. or higher.

6. The cosmetic according to claim 4, wherein a temperature at which loss of the weight of the (co)polymer is 50% in a nitrogen atmosphere is 360 degrees C. or higher.

7. The cosmetic according to claim 3, wherein an amount of an impurity monomer(s) is 100 ppm or less, based on a total weight of the (co)polymer and the monomer(s).

8. The cosmetic according to claim 4, wherein an amount of an impurity monomer(s) is 100 ppm or less, based on a total weight of the (co)polymer and the monomer(s).

* * * * *